(12) United States Patent
Honma et al.

(10) Patent No.: US 6,479,621 B2
(45) Date of Patent: Nov. 12, 2002

(54) POLYHYDROXYALKANOATE CONTAINING 3-HYDROXYTHIENYLALKANOIC ACID AS MONOMER UNIT AND METHOD FOR PRODUCING THE SAME

(75) Inventors: Tsutomu Honma, Atsugi (JP); Tetsuya Yano, Atsugi (JP); Shin Kobayashi, Kawasaki (JP); Takeshi Imamura, Chigasaki (JP); Takashi Kenmoku, Fujisawa (JP); Shinya Kozaki, Shin-machi (JP)

(73) Assignee: Canon Kabushiki Kaisha, Tokyo (JP)

( * ) Notice: Subject to any disclaimer, the term of this patent is extended or adjusted under 35 U.S.C. 154(b) by 78 days.

(21) Appl. No.: 09/793,920

(22) Filed: Feb. 28, 2001

(65) Prior Publication Data

US 2002/0065389 A1 May 30, 2002

(30) Foreign Application Priority Data

Feb. 29, 2000 (JP) ........................ 2000-054317
Feb. 29, 2000 (JP) ........................ 2000-054667

(51) Int. Cl.$^7$ ............................ C08G 63/06; C12P 7/62
(52) U.S. Cl. .................. 528/361; 528/377; 528/380; 527/300; 525/437; 435/41; 435/117; 435/130; 435/135; 435/136; 435/146; 435/874; 435/877
(58) Field of Search .................. 528/361, 377, 528/380; 527/300; 525/437; 435/41, 117, 130, 135, 136, 146, 874, 877

(56) References Cited

U.S. PATENT DOCUMENTS

| | | | |
|---|---|---|---|
| 4,393,167 A | 7/1983 | Holmes et al. | 525/64 |
| 4,876,331 A | 10/1989 | Doi | 528/361 |
| 5,292,860 A | 3/1994 | Shiotani et al. | 528/361 |
| 5,334,698 A | 8/1994 | Wiltholt et al. | 528/354 |
| 2002/0065389 A1 * | 5/2002 | Honma et al. | 528/361 |

FOREIGN PATENT DOCUMENTS

| | | |
|---|---|---|
| JP | 5-49487 | 3/1993 |
| JP | 5-64591 | 3/1993 |
| JP | 5-93049 | 4/1993 |
| JP | 5-214081 | 8/1993 |
| JP | 6-15604 | 3/1994 |
| JP | 6-145311 | 5/1994 |
| JP | 6-284892 | 10/1994 |
| JP | 7-48438 | 2/1995 |
| JP | 7-14352 | 9/1995 |
| JP | 7-265065 | 10/1995 |
| JP | 8-89264 | 4/1996 |
| JP | 2642937 | 5/1997 |
| JP | 9-191893 | 7/1997 |
| JP | 11-32789 | 2/1999 |
| JP | 2989175 | 12/1999 |

OTHER PUBLICATIONS

Curley, et al.; "Production of Poly(3–hydroxyalkanoates) Containing Aromatic Substituents by *Pseudomonas oleovorans*"; Macromolecules, 29, (1996) 1762–1766.

Kim, et al.; "Poly–3–hydroxyalkanoates Produced from *Pseudomonas oleovorans* Grown with ω–Phenoxyalkanoates"; Macromolecules, 29, (1996) 3432–3435.

Andújar, et al.; "Polyesters Produced by *Pseudomonas oleovorans* Containing Cyclohexyl Groups"; Macromolecules, 30, (1997) 1611–1615.

Aróstegui, et al.; "Bacterial Polyesters Produced by *Pseudomonas oleovorans* Containing Nitrophenyl Groups"; Macromolecules, 32, (1999) 2889–2895.

(List continued on next page.)

Primary Examiner—Samuel A. Acquah
(74) Attorney, Agent, or Firm—Fitzpatrick, Cella, Harper & Scinto

(57) ABSTRACT

Microorganisms capable of synthesizing novel polyhydroxyalkanoate having 3-hydroxythienylalkanoic acid as monomer unit, using thienylalkanoic acid as a stock are cultured on a culture medium containing thienylalkanoic acid, and the polyhydroxyalkanoate produced in the cultured cell is extracted and

28 Claims, 4 Drawing Sheets

OTHER PUBLICATIONS

Fritzsche, et al.; "An unusual bacterial polyester with a phenyl pendant group"; Makromol. Chem. 191, (1990) 1957–1965.

Ritter, et al.; Poly(3–hydroxy–5–phenoxypentanoate–co–3–hydroxy–9–phenoxy–nonanoate) from *Pseudomonas oleovorans*; Macromol. Chem. Phys. 195, (1994) 1665–1672.

Derwent Abstract, WPI, No. 1993–137938 for JP 5–074492.

Reháková, et al.; Depolymerization reactions of hyaluronic acid in solution; Int. J. Biol. Macromol., 16, 3 (1994) 121–124.

Lytle, et al.; "Filtration Sizes of Human Immunodeficiency Virus Type 1 and Surrogate Viruses Used To Test Barrier Materials"; Appl. and Environ. Microb., 58, 2, (1992) 747–749.

Kim, et al.; "Preparation and Characterization of Poly (β–hydroxyalkanotates) Obtained from *Pseudomonas oleovorans* Grown with Mixtures of 5–Phenylvaleric Acid and n–Alkanoic Acids"; Macromolecules, 24, (1991) 5256–5260.

* cited by examiner

SEQUENCE LISTING

<160> NUMBER OF SEQ ID NOS: 1

<210> SEQ ID NO 1
<211> LENGTH: 1501
<212> TYPE: DNA
<213> ORGANISM: Pseudomonas jessenii 161 strain.

<400> SEQUENCE: 1

```
tgaacgctgg cggcaggcct aacacatgca agtcgagcgg atgacgggag cttgctcctg      60
aattcagcgg cggacgggtg agtaatgcct aggaatctgc ctggtagtgg gggacaacgt     120
ctcgaaaggg acgctaatac cgcatacgtc ctacgggaga aagcagggga ccttcgggcc     180
ttgcgctatc agatgagcct aggtcggatt agctagttgg tgaggtaatg gctcaccaag     240
gcgacgatcc gtaactggtc tgagaggatg atcagtcaca ctgaactga gacacggtcc      300
agactcctac gggaggcagc agtggggaat attggacaat gggcgaaagc ctgatccagc     360
catgccgcgt gtgtgaagaa ggtcttcgga ttgtaaagca ctttaagttg ggaggaaggg     420
cattaaccta atacgttagt gttttgacgt taccgacaga ataagcaccg gctaactctg     480
tgccagcagc cgcggtaata cagagggtgc aagcgttaat cggaattact gggcgtaaag     540
cgcgcgtagg tggtttgtta agttggatgt gaaagccccg ggctcaacct gggaactgca     600
ttcaaaactg acaagctaga gtatggtaga gggtggtgga atttcctgtg tagcggtgaa     660
atgcgtagat ataggaagga acaccagtgg cgaaggcgac cacctggact gatactgaca     720
ctgaggtgcg aaagcgtggg gagcaaacag gattagatac cctggtagtc cacgccgtaa     780
acgatgtcaa ctagccgttg ggagccttga gctcttagtg cgcagctaa cgcattaagt      840
tgaccgcctg gggagtacgg ccgcaaggtt aaaactcaaa tgaattgacg ggggcccgca     900
caagcggtgg agcatgtggt ttaattcgaa gcaacgcgaa gaaccttacc aggccttgac     960
atccaatgaa ctttccagag atggatgggt gccttcggga acattgagac aggtgctgca    1020
tggctgtcgt cagctcgtgt cgtgagatgt tgggttaagt cccgtaacga gcgcaaccct    1080
tgtccttagt taccagcacg taatggtggg cactctaagg agactgccgg tgacaaaccg    1140
gaggaaggtg gggatgacgt caagtcatca tggcccttac ggcctgggct acacacgtgc    1200
tacaatggtc ggtacagagg gttgccaagc cgcgaggtgg agctaatccc acaaaaccga    1260
tcgtagtccg gatcgcagtc tgcaactcga ctgcgtgaag tcggaatcgc tagtaatcgc    1320
```

-continued

```
gaatcagaat gtcgcggtga atacgttccc gggccttgta cacaccgccc gtcacaccat    1380
gggagtgggt tgcaccagaa gtagctagtc taaccttcgg gaggacggtt accacggtgt    1440
gattcatgac tggggtgaag tcgtaccaag gtagccgtag gggaacctgc ggctggatca    1500
c                                                                   1501
```

POLYHYDROXYALKANOATE CONTAINING 3-HYDROXYTHIENYLALKANOIC ACID AS MONOMER UNIT AND METHOD FOR PRODUCING THE SAME

BACKGROUND OF THE INVENTION

Field of the Invention

The present invention relates to a novel polyhydroxyalkanoate (may be abbreviated as PHA, hereinafter). Also, it relates to a very effective method for manufacturing such PHA using microorganisms capable of producing PHA and accumulating it in the cell.

Hitherto, many microorganisms have reportedly produced poly-3-hydroxybutyric acid (may be abbreviated as PHB) or other PHAs and accumulated them in the cell ("Biodegradation Plastic Handbook", Biodegradable Plastic Research Association, NTS, Co. Ltd., P178–197). As in the case of conventional plastics, these polymers can be used for producing various kinds of products through melt processing and the like. Furthermore, since they are biodegradable they are advantageously degraded completely by microorganisms in the natural world, and do not remain in the natural environment to cause pollution unlike many conventional synthetic polymers. Also, they have good biocompatibility, and applications as medical soft materials and the like are expected.

It is known that these PHAs may have various compositions and structures depending on types of microorganisms for use in production thereof and culture medium compositions, culture conditions and the like, and until now, studies have been made on control of these compositions and structures, principally in terms of improvement of properties of PHA.

For example, it has been reported that *Alcaligenes eutropus* H16, ATCC No. 17699 and its mutants produce copolymers of 3-hydroxybutyric acid (may be abbreviated as 3HB, hereinafter) and 3-hydroxyvaleric acid (may be abbreviated as 3HV) in various composition ratios, by changing carbon sources during their culture (Japanese Patent Application Publication (Kokoku) No. 6-15604, Japanese Patent Application Publication (Kokoku) No. 7-14352, Japanese Patent Application Publication (Kokoku) No. 8-19227).

In Japanese Patent Application Laid-Open No. 5-74492, a method in which the copolymer of 3HB and 3HV is produced by bringing Methylobacterium sp., Paracoccus sp., Alcaligenes sp. and Pseudomonas sp. into contact with primary alcohol having three to seven carbons is disclosed.

In Japanese Patent Application Laid-Open No. 5-93049 and Japanese Patent Application Laid-Open No. 7-265065, it is disclosed that binary copolymers of 3HB and 3-hydroxyhexanoic acid (may be abbreviated as 3HHx, hereinafter) are produced by culturing *Aeromonas caviae*) with oleic acid or olive oil as carbon sources.

In Japanese Patent Application Laid-Open No. 9-191893, it is disclosed that *Comamonas acidovoranas* IFO 13852 produces polyester having 3HB and 4-hydroxybutyric acid as monomer unit through culture using gluconic acid and 1,4-butandiol as carbon sources.

Also, currently, studies are vigorously carried out as to PHA composed of 3-hydroxyalkanoate (may be abbreviated as 3HA hereinafter) of medium-chain-length: abbreviated as mcl) having up to about twelve carbons. Synthetic pathways of PHA can be classified broadly into two types, and specific examples thereof will be shown in the following (1) and (2).

(1) Synthesis using β oxidation

In Japanese Patent No. 2642937, it is disclosed that PHA having monomer unit of 3-hydroxyalkanoate having six to twelve carbons is produced by giving acyclic aliphatic hydrocarbons as carbon sources to *Pseudomonas oleovorans* ATCC 29347. Also, in Appl. Environ. Microbiol, 58 (2), 746 (1992), it is reported that *Pseudomonas resinovorans* produces polyester having 3-hydroxybutyric acid, 3-hydroxyhexanoic acid, 3-hydroxyoctanoic acid and 3-hydroxydecanoic acid (amount ratio 1:15:75:9) as monomer unit, with octanoic acid as a sole carbon source, and produces polyester having 3-hydroxybutyric acid, 3-hydroxyhexanoic acid, 3-hydroxyoctanoic acid and 3-hydroxudecanoic acid (amount ratio 8:62:23:7) as monomer unit, with hexanoic acid as a sole carbon source. Here, it is believed that the 3HA monomer unit having chain length larger than that of stock fatty acid are by way of fatty acid synthetic pathway that is described in (2).

(2) Synthesis using fatty acid synthesis routs

In Int. J. Biol. Macromol., 16 (3), 119 (1994), it is reported that Pseudomonas sp.61-3 strain produces polyester having as monomer unit 3-hydroxyalkanoic acids such as 3-hydroxybutyric acid, 3-hydroxyhexanoic acid, 3-hydroxyoctanoic acid, 3-hydroxydecanoic acid and 3-hydroxydodecanoic acid, and 3-hydroxyalkenoic acids such as 3-hydroxy-5-cis-decenoic acid and 3-hydroxy-5-cis-dodecenoic acid, with sodium gluconate as a sole carbon source.

By the way, biosynthesis of PHA is usually performed by PHA synthase using as a matrix "D-3-hydroxyacyl-CoA" produced as intermediates of various metabolism pathways in cells.

Here, "CoA" refers to "coenzyme A". And, as described in the above prior art of (1), if using fatty acids such as octanoic acid and nonanoic acid as carbon sources, the biosynthesis of PHA is performed with "D-3-hydroxyacyl-CoA" produced in the "β-oxidation cycle" as a starting substance.

Reactions through which PHA is biosynthesized by way of the "β-oxidation cycle" are shown in the following.

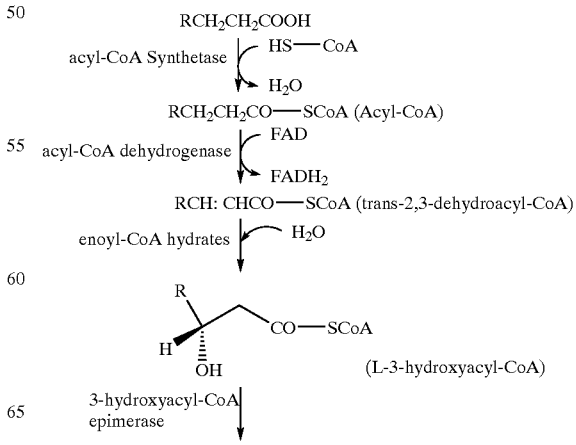

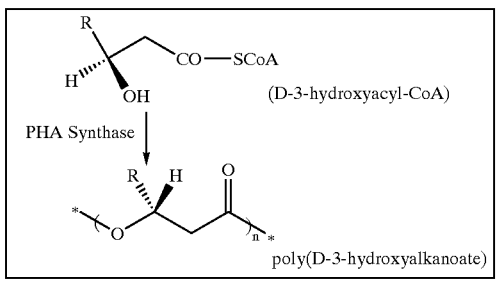

On the other hand, as described in the above prior art of (2), if PHA is biosynthesized using saccharides such as glucose, the biosynthesis is performed using the "D-3-hydroxyacyl-CoA" converted from "D-3-hydroxyacyl-ACP" produced in the "fatty acid synthetic pathway" as start substance.

Here, "ACP" refers to "acyl carrier protein".

By the way, as described previously, both any PHA being synthesized in above (1) and (2) is PHA composed of monomer unit having alkyl groups on the side chain, that is "usual PHA". However, if considering more widespread application of microorganism producible PHA like this, for example application as functional polymers, it is expected that PHA having substituents other than alkyl groups (e.g. phenyl groups) incorporated in the side chain is extremely useful. Examples of other substituents include unsaturated hydrocarbons, ester groups, allyl groups, cyano groups, halogenated hydrocarbons and epoxide.

For synthesis of PHA having such substituents incorporated therein (hereinafter, referred to as "unusual PHA" as necessary), for example, a report as to PHA having aryl groups and the like in terms of synthesis using β oxidation is found in Macromolecules, 24, p 5256–5260 (1991). Specifically, it is reported that *Pseudomonas oleovorans* produces 160 mg of PHA per liter of culture medium (the ratio of dry weight to the cell is 31.6%), containing as monomer unit 3HV, 3-hydroxyheptanoic acid, 3-hydroxynonanoic acid, 3-hydroxyundecanoic acid and 3-hydroxy-5-phenylvaleric acid (may be abbreviated as 3HPV, hereinafter) in the amount ratio of 0.6:16.0:41.1:1.7:40.6 using 5-phenylvaleric acid (may be abbreviated as PVA) and nonanoic acid (mole ratio of 2:1 and total concentration of 10 mmol/L), and produces 200 mg of PHA per liter of culture medium (the ratio of dry weight to the cell mass is 39.2%), containing as monomer unit 3HHx, 3-hydroxyoctanoic acid, 3-hydroxydecanoic acid and 3HPV in the amount ratio of 7.3:64.5:3.9:24.3 using PVA and octanoic acid (mole ration of 1:1, and total concentration of 10 mmol/L). It is thought that PHA in this report is synthesized principally by way of the β-oxidation from the fact that nonanoic acid and octanoic acid are used.

Related descriptions are also found in Macromol. Chem., 191, 1957–1965 (1990) and Chirality, 3, 492–494 (1991), and the change of polymer properties that is probably caused by contained 3HPV is recognized.

As described above, for microorganism producible PHA, those having various kinds of compositions and structures have been obtained by varying types of microorganisms for use in their production, culture compositions, culture conditions and the like, but they cannot be appropriate yet in terms of properties when their application as plastics is considered. In order to further expand the application range of microorganism producible PHA, it is important to consider the improvement of properties more widely, and for this purpose, research and development of PHA containing monomer unit having more diversified structures, methods for production thereof, and microorganisms capable of producing desired PHA effectively are essential.

On the other hand, for PHA having substituents incorporated in the side chain (unusual PHA) as described above, incorporated substituents are selected in accordance with desired properties and the like, whereby development as "functional polymers" having very useful functions and properties resulting from properties of incorporated substituents and the like can also be expected, and research and development of excellent PHA allowing such functionality and biodegradability to be compatible with each other, methods for production thereof, and microorganisms capable of producing desired PHA efficiently are also important challenges.

Other examples of PHA having these substituents incorporated in the side chain include PHAs having phenyl groups, and phenoxy groups on the side chain.

As another example of phenyl groups, it is reported that *Pseudomonas oleovorans* produces PHA containing 3-hydroxy-5-(4-tril) valeric acid as monomer unit through culture on a medium containing 5-(4-tril) valeric acid (5-(4-methylphenyl) valeric acid), in Macromolecules, 29, 1762–1766 (1996).

Furthermore, in Macromolecules, 32, 2889–2895 (1999), it is reported that *Pseudomonas oleovorans* produces PHA containing 3-hydroxy-5-(2,4-dinitrophenyl) valeric acid and 3-hydroxy-5-(4-nitrophenyl) valeric acid as monomer unit through culture on a medium containing 5-(2,4-dinitrophenyl) valeric acid and nonanoic acid.

Also, as an example of phenoxy groups, it is reported that Pseudomonas oleovorans produces PHA containing 3-hydroxy-5-phenoxyvaleric acid and 3-hydroxy-9-phenoxynonanoic acid as units from 11-phenoxyundecanoic acid, in Macromol. Chem. Phys., 195, 1665–1672 (1994).

Also, in Macromolecules, 29, 3432–3435 (1996), it is reported that using *Pseudomonas oleovorans*, PHA containing 3-hydroxy-4-phenoxybutyric acid and 3-hydroxy-6-phenoxyhexanoic acid as units is produced from 6-phenoxyhexanoic acid, PHA containing 3-hydroxy-4-phenoxybutyric acid, 3-hydroxy-6-phenoxyhexanoic acid and 3-hydroxy-8-phenoxyoctanoic acid as units is produced from 8-phenoxyoctanoic acid, and PHA containing 3-hydroxy-5-phenoxyvaleric acid and 3-hydroxy-7-phenoxyheptanoic acid as units is produced from 11-phenoxyundecanoic acid. Yields of polymers in this report are extracted and are shown in the following.

| Carbon sources (Alkanoate) | Dry weight of cells (mg/L) | Dry weight of polymers (mg/L) | Yields (%) |
|---|---|---|---|
| 6-phenoxyhexanoic acid | 950 | 100 | 10.5 |
| 8-phenoxyoctanoic acid | 820 | 90 | 11 |
| 11-phenoxyundecanoic acid | 150 | 15 | 10 |

Furthermore, in Can. J. Microbiol., 41, 32–43 (1995), PHA containing 3-hydroxy-p-cyanophenoxyhexanoic acid or 3-hydroxy-p-nitrophenoxyhexanoic acid as monomer unit is successfully produced with octanoic acid and p-cyanophenoxyhexanoic acid or p-nitrophenoxyhexanoic acid as a raw material, using *Pseudomonas oleovorans* ATCC 29347 and *Pseudomonas putida* KT 2442.

In Japanese Patent No. 2989175, methods of producing a homopolymer composed of 3-hydroxy-5-(monofluorophenoxy)pentanoate (may be abbreviated as 3H5(MFP)P, hereinafter) units or 3-hydroxy-5-(difluorophenoxy)pentanoate (may be abbreviated as 3H5 (DFP)P, hereinafter) units and a copolymer containing at least 3H5(MFP)P units or 3H5 (DFP) P units; *Pseudomonas putida* for synthesizing these polymers; and the above described polymers using Pseudomonas sp. are described.

These productions are performed through "two-stage culture" as described below.
Culture time: first stage, 24 hours ; second stage, 96 hours
Carbon sources and obtained polymers in respective stages are shown below.
(1) Obtained polymer: 3H5 (MFP)P homopolymer
 Carbon sources in the first stage: citric acid, yeast extract
 Carbon source in the second stage: monofluorophenoxyundecanoic acid
(2) Obtained polymer: 3H5 (DFP)P homopolymer
 Carbon sources in the first stage: citric acid, yeast extract
 Carbon source in the second stage: difluorophenoxyundecanoic acid
(3) Obtained polymer: 3H5 (MFP) P copolymer
 Carbon sources in the first stage: octanoic acid or nonanoic acid, and yeast extract
 Carbon source in the second stage: monofluorophenoxyundecanoic acid
(4) Obtained polymer: 3H5 (DFP) P copolymer
 Carbon sources in the first stage: octanoic acid or nonanoic acid, and yeast extract
 Carbon source in the second stage: difluorophenoxyundecanoic acid For the effect, fatty acid of medium-chain-length having substituents can be materialized to synthesize a polymer having phenoxy groups with chain ends substituted by one to two fluorine atoms, and stereoregularity and water repellency can be given while maintaining high melting points and good processability.

Also, it is expected that PHA containing cyclohexyl groups in the monomer unit exhibits polymer properties different from those of PHA containing usual aliphatic hydroxyalkanoic acid as units, and an example of its production by *Pseudomonas oleovorans* has been reported (Macromolecules, 30, 1611–1615 (1997)).

According to this report, when *Pseudomonas oleovorans* was cultured in a medium where nonanoic acid (may be abbreviated as NA, hereinafter) and crylohexylbutyric acid (may be abbreviated as CHBA, hereinafter) or cyclohexylvaleric acid (may be abbreviated as CHVA, hereinafter) coexisted, PHA containing units containing cyclohexyl groups and units derived from nonanoic acid was obtained (each ratio is unknown).

For its yields and the like, it has been reported that the amount ratio between CHBA and NA was changed with total concentration of 20 mmol/L to obtain results as shown in the following.

| NA:CHBA | CDW | PDW | Yields | Units |
|---|---|---|---|---|
| 5:5 | 756.0 | 89.1 | 11.8 | NA, CHBA |
| 1:9 | 132.8 | 19.3 | 14.5 | NA, CHBA |

CDW: Dry weight of cells (mg/L)
PDW: Dry weight of polymers (mg/L)
Yield: PDW/CDW (%)

In this example, however, the yield of polymers for culture medium is not enough, and obtained PHA itself has also aliphatic hydroxyalkanoic acid derived from nonanoic acid coexisting in its monomer unit.

In this way, in the case where PHA having various substituents incorporated in the side chain is to be produced using microorganisms, methods in which alkanoate having substituents to be incorporated is used not only as polymer material but also as a carbon source for growth are used, as found in the reported examples of *Pseudomonas oleovorans* described previously.

However, in the method in which alkanoate having substituents to be incorporated is used not only as polymer material but also as a carbon source for growth, the supply of an energy source on the basis of production of acetyl-CoA through β-oxidation from the alkanoate is expected, and in this method, acetyl-CoA cannot be produced through β oxidation unless starting substance having a certain degree of chain length are used, and alkanoate that can be used as a row material of PHA is thus limited, which is a major problem. Also, since matrixes with chain length reduced by two methylene chains are newly produced through β-oxidation and they are incorporated as monomer unit of PHA, PHA that is synthesized is often a copolymer composed of monomer unit with chain lengths different by two methylene chains. In the reported example described above, a copolymer composed of three kinds of monomer unit of 3-hydroxy-8-phenoxyoctanoic acid derived from 8-phenoxyoctanoic acid, and 3-hydroxy-6-phenoxyhexanoic acid and 3-hydroxy-4-phenoxybutyric acid, which are by-products derived from metabolites is produced. In this respect, in the case of obtaining PHA composed of single monomer unit, it is extremely difficult to use this method. Furthermore, in methods based on the supply of energy sources on the basis of production of acetyl-CoA through β-oxidation, the growth of microorganisms is slow and thus much time is required for synthesis of PHA, and yields of synthesized PHA tends to be lower, which is also a major problem.

Thus, methods in which microorganisms are cultured on a medium where fatty acids of medium-chain-length such as octanoic acid and nonanoic acid and so forth coexist as a carbon source for growth in addition to alkanoate having substituents to be incorporated, and then PHA is extracted are considered effective, and are generally used.

However, according to considerations by the present inventors, PHA synthesized by way of the β-oxidation pathway using fatty acids of medium-chain-length such as octanoic acid and nonanoic acid and so on as a carbon source for growth has lower purity, and 50% or more of obtained polymers are mcl-3HA monomer unit that are monomer unit derived from the carbon source for growth (for example, 3-hydroxyoctanoic acid and 3-hydroxynonanoic acid), namely units of "usual PHA". These mcl-3HA units are sticky polymers at room temperature in the case of single composition, and if they coexist in large quantity in PHA intended by the present invention, the glass transition temperature (Tg) of the polymer is significantly decreased. Thus, when hard polymer properties are to be obtained at room temperature, the coexistence of the mcl-3HA monomer unit is not desirable. Also, a hetero side chain structure like this is known to hinder interaction derived from the intramolecular or intermolecular side chain structure and have a significant influence on crystalline and orientation. For achieving improvement of polymer properties and addition of new functions, the coexistence of these mcl-3HA monomer unit is a major problem. As means for solving this problem, a purification process for separating and removing "undesired" monomer unit such as mcl-3HA monomer unit derived from the carbon source for growth is provided to obtain PHA composed of only monomer unit having specific substituents. However, the problem is that operations become complicated and significant reduction of yields cannot be avoided. The more serious problem is that it is extremely difficult to remove only undesired monomer unit when desired monomer unit and undesired monomer unit form a copolymer. In particular, when the object is to synthesize PHA containing monomer unit having groups obtained from unsaturated hydrocarbons, ester groups, allyl groups, cyano groups, nitro groups, groups obtained from halogenated hydrocarbons, and groups with epoxide, etc. incorporated therein as a side chain, there are many cases where the mcl-3HA monomer unit forms a copolymer with the desired monomer unit, and the removal of the mcl-3HA monomer unit after synthesis of PHA is thus extremely difficult.

Thus, the present inventors have reached recognition that development of a biosynthetic method by which "unusual PHA" can be obtained in high purity is absolutely necessary when considering application to functional polymers. Therefore, it has been thought that development of excellent polymers having both functionality and biodegradability and microorganisms capable of producing such polymers and accumulating them in the cell as described above, and a method for efficiently biosynthesizing such PHA in high purity is quite useful and important.

SUMMARY OF THE INVENTION

The present invention solves the above described problems, and is to provide PHA containing monomer unit of diversified structures having in the side chain substituents useful as device material and medical material (unusual PHA) and provide a method of producing such "unusual PHA" using microorganisms, and in particular, provide a producing method in which coexisting undesired monomer unit are reduced and desired "unusual PHA" can be thus obtained in high purity, and in addition, high fields are achieved.

Thus, the present inventors have continued to carry out enthusiastic studies on screening of microorganisms capable of producing various kinds of PHA and accumulating them in the cell and a method of producing desired PHA using these microorganisms, with the aim of developing PHA having in the side chain functional groups useful as device material and medical material. As a result, we have found microorganisms capable of producing novel PHA containing as monomer unit 3-hydroxythienylalcanoic acid represented by Chemical Formula [2],

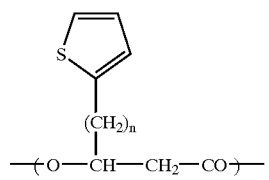

[2]

(n is any one of integers of 1 to 8) using as a stock thienylalkanoic acid represented by Chemical Formula [9],

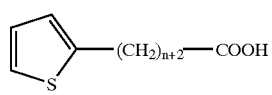

[9]

(n is any one of integers of 1 to 8) and accumulating the same in the cell, and in addition, we have found that such PHA can be biosynthesized by culturing these microorganisms under coexistence of thienylalkanoic acid represented by the above described Chemical Formula [9] and saccharides, yeast extract or polypeptone, and that the PHA obtained thereby has higher purity.

More particularly, we have found microorganisms capable of producing novel PHA containing as monomer unit 3-hydroxy-4-(2-thienyl) butyric acid (hereinafter abbreviated as 3HTB) represented by Chemical Formula [5],

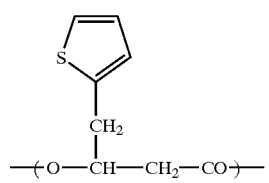

[5]

3-hydroxy-5-(2-thienyl) valeric acid (hereinafter abbreviated as 3HTV) represented by Chemical Formula [6],

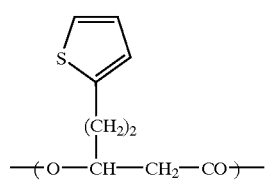

[6]

3-hydroxy-6-(2-thienyl) hexanoic acid (hereinafter abbreviated as 3HTHx) represented by Chemical Formula [7],

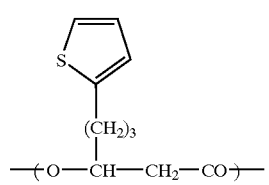

[7]

and 3-hydroxy-7-(2-thienyl) heptanoic acid (hereinafter abbreviated as 3HTHp) represented by Chemical Formula

[8],

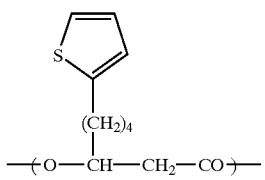

using as stocks at least any one of 5-(2-thienyl) valeric acid (hereinafter abbreviated as TVA) represented by Chemical Formula [11],

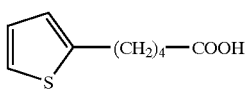

6-(2-thienyl) hexanoic acid (hereinafter abbreviated as THxA) represented by Chemical Formula [12],

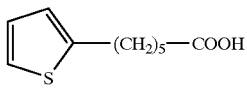

7-(2-thienyl) heptanoic acid (hereinafter abbreviated as THpA) represented by Chemical Formula [13],

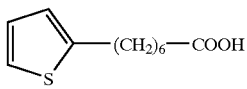

and accumulating the same in the cell, and in addition we have found that such PHA can be biosynthesized by culturing these microorganisms under coexistence of TVA, THxA or THpA and saccharides, yeast extract or polypeptone, and that the PHA obtained thereby has higher purity, resulting in the present invention.

That is, the present invention relates to polyhydroxyalkanoate having monomer unit represented by Chemical Formula [2]

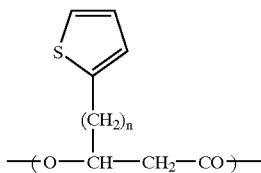

(n is any one of integers of 1 to 8).

Also, the present invention relates to a method of producing the PHA, characterized by having a process in which microorganisms are cultured on a culture medium containing thienylalkanoic acid represented by Chemical formula [9],

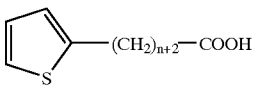

(n is any one of integers of 1 to 8), thereby making such microorganisms produce PHA having corresponding monomer unit represented by the above described Chemical Formula [10],

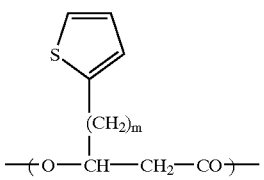

(wherein in the above formula, m is one or more selected from the group consisting of n, n–2, n–4 and n–6, and also an integer greater than or equal to 1).

That is, the method of producing PHA according to the present invention is characterized by having a process of culturing microorganisms producing PHA containing 3HTB, 3HTV, 3HTHx or 3HTHp as monomer unit under the coexistence of TVA, THxA or THpA and saccharides, yeast extract or polypeptone.

According to the present invention, new polyhydroalkanoate having monomer unit represented by the above described Chemical Formula [1], and a method of producing the polyhydroalkanoate using microorganisms are provided. By this, the polyhydroalkanoate useful as a functional polymer can be efficiently produced, and its application to various fields such as device material and medical material can be expected.

According to the present invention, it is made possible to provide PHA (unusual PHA) containing monomer unit of diversified structures having on the side chain substituents useful as device material, medical material and the like, and provide a method of producing the "unusual PHA" using microorganisms. Particularly, a method in which undesired monomer unit are reduced and thus desired "unusual PHA" can be obtained in high purity, and high yields are achieved can be provided.

DETAILED DESCRIPTION OF THE PREFERRED EMBODIMENTS

Figure 1:
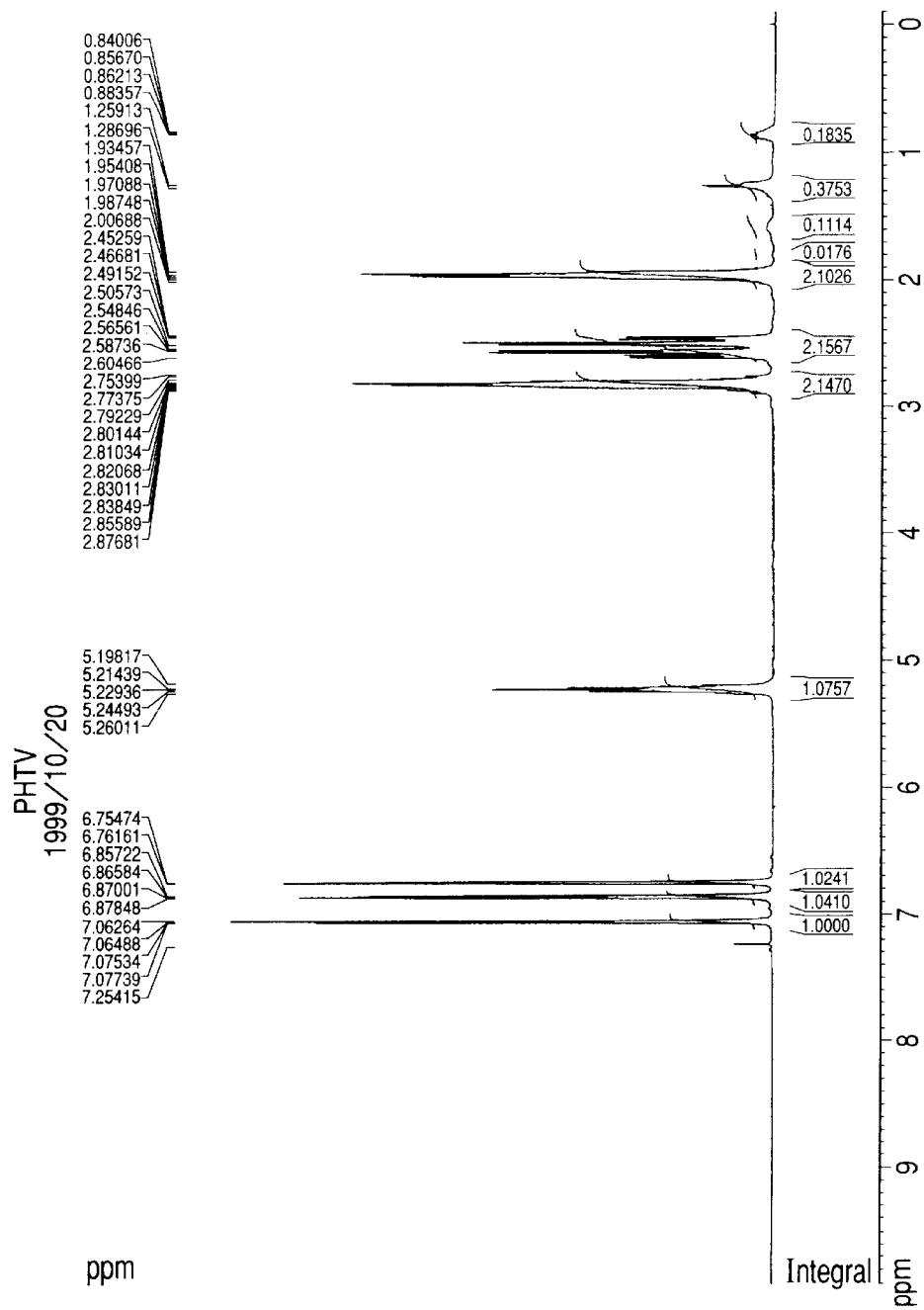
FIG. 1 illustrates a $^1$H-NMR spectrum of a polymer using TVA as a raw material in Example 1.

The PHA of the present invention is PHA containing monomer unit of diversified structures having on the side chain substituents useful for device material, medical material and the like, more specifically PHA having thienyl groups on the side chain. Also, the method of producing PHA according to the present invention makes it possible to produce desired PHA in high purity and high yields using microorganisms. Furthermore, the PHA of the present invention is isotactic polymers that are generally composed of only R bodies.

Saccharides Differences from Prior Arts

One of the methods of producing PHA according to the present invention is characterized in that not only alkanoic acid for incorporating desired monomer unit but also only saccharides as a carbon source other than the alkanoic acid are added in a culture medium when microorganisms are cultured, thereby significantly increasing the content of desired monomer unit or giving only desired monomer unit in PHA produced and accumulated by microorganisms. The effect of fostering the assignment of high priority to specific monomer unit is achieved by adding only saccharides in the culture medium as a carbon source other than the alkanoic acid.

That is, the present inventors performed culture, using saccharides as coexisting carbon sources together with alkanoic acid for incorporating desired monomer unit, and consequently arrived at findings that desired PHA is obtained in much higher yields and purity compared to conventional methods using mcl-alkanoic acid such as nonanoic acid and octanoic acid as coexisting carbon sources, and this effect is achieved by the culturing method capable of producing acetyl-CoA that is a carbon source and energy source for microorganisms by means of a process not using β-oxidation, thus resulting in the present invention.

In the method of the present invention, saccharides compounds such as glucose, fructose and mannose are used as growth carbon source for microorganisms, and PHA that is produced is composed of alkanoate for incorporating desired monomer unit, which is made to coexist with saccharides, and contains no or very little monomer unit derived from saccharides such as glucose. In this respect, the method of the present invention is fundamentally different in configuration and effect from conventional PHA microorganism producing methods using saccharides themselves such as glucose as starting materials for monomer unit that are incorporated in PHA.

Yeast Extract Differences from Prior Arts

One of the methods of producing PHA according to the present invention is characterized in that not only alkanoic acid for incorporating desired monomer unit but also only yeast extract as a carbon source other than the alkanoic acid are added in a culture medium when microorganisms are cultured, thereby significantly increasing the content of desired monomer unit or giving only desired monomer unit in PHA produced and accumulated by microorganisms. The effect of fostering the assignment of high priority to specific monomer unit is achieved by adding only yeast extract in the culture medium as a carbon source other than the alkanoic acid.

An example of using yeast extract in the culture medium at the time of producing PHA by microorganisms is a method in which microorganisms classified as Rhodobacter sp. are used, as described in Japanese Patent Application Laid-Open No. 5-49487. However, this conventional method is a method of producing general PHB and PHV having as monomer unit hydroxyalkanoate having no substituents. A synthetic pathway as intended by the present invention is known to be a pathway independent of synthetic pathways through which PHB and PHV are produced, and in Japanese Patent Application Laid-Open No. 5-49487, there is no description about the effect of yeast extract in the synthetic pathway of PHA as intended by the present invention. Also, for the effect of yeast extract, it is only shown in terms of PHA and PHV generally produced by microorganisms that addition of yeast extract will simply increase the amount of accumulated PHA in the cell, and it is clearly stated that yeast extract is not added for the purpose of growth. The present invention is to perform production and accumulation as well as growth by making thienylalkanoic acid and yeast extract coexist, and is thus utterly different therefrom. Furthermore, there is no description about assignment of high priority to specific monomer unit, which is an effect of the present invention, and unlike the present invention, the effect of assignment of high priority to specific monomer unit having thienyl groups as substituents in the composition of PHA produced by microorganisms is not shown.

Furthermore, an example of using yeast extract for production of PHA by microorganisms is a method in which *Pseudomonas putida* described in Japanese Patent No. 2989175 is used. The method of producing PHA described here is only a method using two stage culture, and it is disclosed that the accumulation of PHA is performed only in the second-stage culture, under limitation on nutritive sources other than carbon source. In this respect, it is utterly different in configuration and effects from the method in which desired PHA is synthesized and accumulated only through one-stage culture on the culture medium containing thienylalakanoic acid and yeast extract on the present invention. Also, the effect of yeast extract in Japanese Patent No. 2989175 is aimed simply at growth of microorganisms for use in second-stage culture, in the first stage culture, in the case of using two stage culture, and it is clearly stated therein that in the first stage, culture is performed under conditions of abundant nutrient sources. Here, the row material of PHA does not coexist in the first stage. For the effect of yeast extract in the present invention, production and accumulation of PHA as well as growth are performed by making thienylalkanoic acid and yeast extract coexist, which is utterly different in effects brought about by yeast extract. Also, in Japanese Patent No. 2989175, any one of citric acid, octanoic acid and nonanoic acid coexists as a carbon source in the first-stage culture, which is utterly different also in configuration from the present invention where only thienylalakanoic acid and yeast extract are made to coexist.

Polypeptone Differences from Prior Arts

One of the methods of producing PHA according to the present invention is characterized in that not only alkanoic acid for incorporating desired monomer unit but also only polypeptone as a carbon source other than the alkanoic acid are added in a culture medium when microorganisms are cultured, thereby significantly increasing the content of desired monomer unit or giving only desired monomer unit in PHA produced and accumulated by microorganisms. The effect of fostering the assignment of high priority to specific monomer unit is achieved by adding only polypeptone in the culture medium as a carbon source other than the alkanoic acid.

Furthermore, as examples of using polypeptone for the production of PHA by microorganisms, it is disclosed that polypeptone is contained in the culture medium when microorganisms are made to produce PHA in Japanese Patent Application Laid-Open No. 5-49487, Japanese Patent Application Laid-Open No. 5-64591, Japanese Patent Application Laid-Open No. 5-214081, Japanese Patent Application Laid-Open No. 6-145311, Japanese Patent Application Laid-Open No. 6-284892, Japanese Patent Application Laid-Open No. 7-48438, Japanese Patent Application Laid-Open No. 8-89264, Japanese Patent Application Laid-Open No. 9-191893 and Japanese Patent Application Laid-Open No. 11-32789, but in any case, polypeptone is used in a pre-culture stage, namely in a stage for simply growing the cell, and row materials that are monomer unit are not included during pre-culture. Also, there are no examples where polypeptone has been used in the process of making the cell produce PHA. In contrast to this, the present invention is to perform production and accumulation of PHA as well as growth by making alkanoic acid for incorporating desired monomer unit and only polypeptone as a carbon source other than such alkanoic acid coexist, and is utterly different in configuration and effect from conventional examples of using polypeptone. Furthermore, there is no description about assignment of high priority to specific monomer unit, which is an effect of the present invention, and unlike the present invention, the effect of assignment of high priority to specific monomer unit having thienyl groups as substituents in the composition of PHA produced by microorganisms is not shown.

Microorganisms, culture processes and the like for use in the present invention will be described below.

PHA Monomer Unit Feed Systems

First, a "fatty acid synthetic pathway" that is one of feed systems of mcl-3HA monomer unit coming to coexist in desired PHA will be described in detail.

In the case of using saccharides such as glucose as a carbon source, alkanoic acid required as a cell component is biosynthesized from the "fatty acid synthetic pathway" of which starting substance is acetyl-CoA that is produced from saccharides through a "glycolysis system". Furthermore, the fatty acid synthesis involves a new (de novo) synthetic pathway and a carbon chain expansion pathway, and they will be described below.

(1) New (de novo) synthetic pathway

It is catalyzed by two enzymes of an acetyl-CoA carboxylase (EC 6.4.1.2) and a fatty acid synthesis enzyme (EC 2.3.1.85). Furthermore, the acetyl-CoA carboxylase is an enzyme involving biotin, and finally catalyzing the following reaction to produce malonyl-CoA from acetyl-CoA, and the reaction is expressed by the following formula.

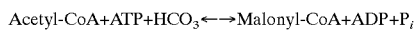

Acetyl-CoA+ATP+HCO$_3^-$ ⇌ Malonyl-CoA+ADP+P$_i$

Also, the fatty acid synthesis enzyme is a enzyme catalyzing the reactive cycle of transfer—condensation—reduction—dehydration—reduction, and the total reaction is expressed by the following formula.

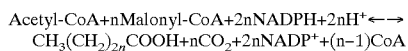

Acetyl-CoA+nMalonyl-CoA+2nNADPH+2nH$^+$ ⇌ CH$_3$(CH$_2$)$_{2n}$COOH+nCO$_2$+2nNADP$^+$+(n−1)CoA Furthermore, depending on types of enzymes, the reaction product may be free acid, a CoA derivative or an ACP derivative.

Here, the acetyl-CoA is expressed by the following chemical formula,

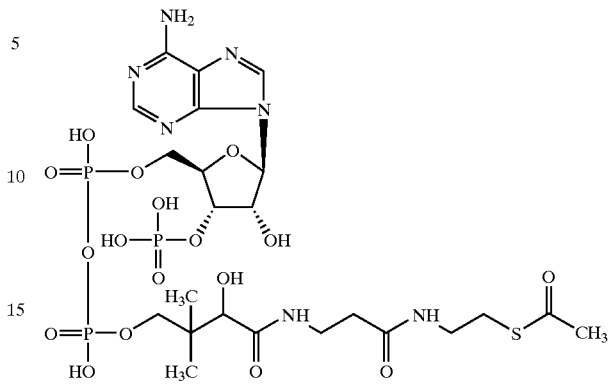

and the malonyl-CoA is expressed by the following chemical formula.

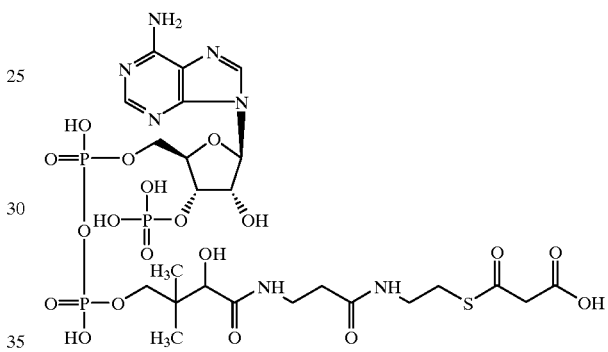

Furthermore, CoA is an abbreviation of coenzyme A, and is expressed by the following chemical formula.

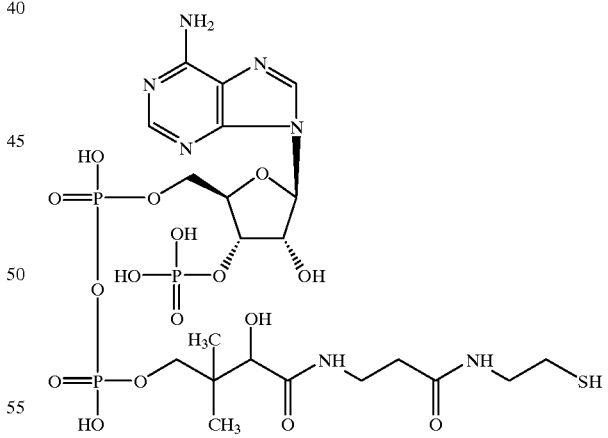

"D-3-hydroxyacyl-ACP" is supplied as an intermediate that is a monomer substrate for biosynthesis of PHA through the following pathway in these pathways. Also, as shown in the following reaction formula, the pathway continues to add carbons on a two-by-two basis and is finally extended to palmitic acid. Therefore, for the monomer substrate for biosynthesis of PHA, seven types of "D-3-hytroxyacyl-ACP" of "D-3-hydroxybutyryl-ACP" to "D-3-hydroxypalmitil-ACP" having even numbers of carbons are supplied.

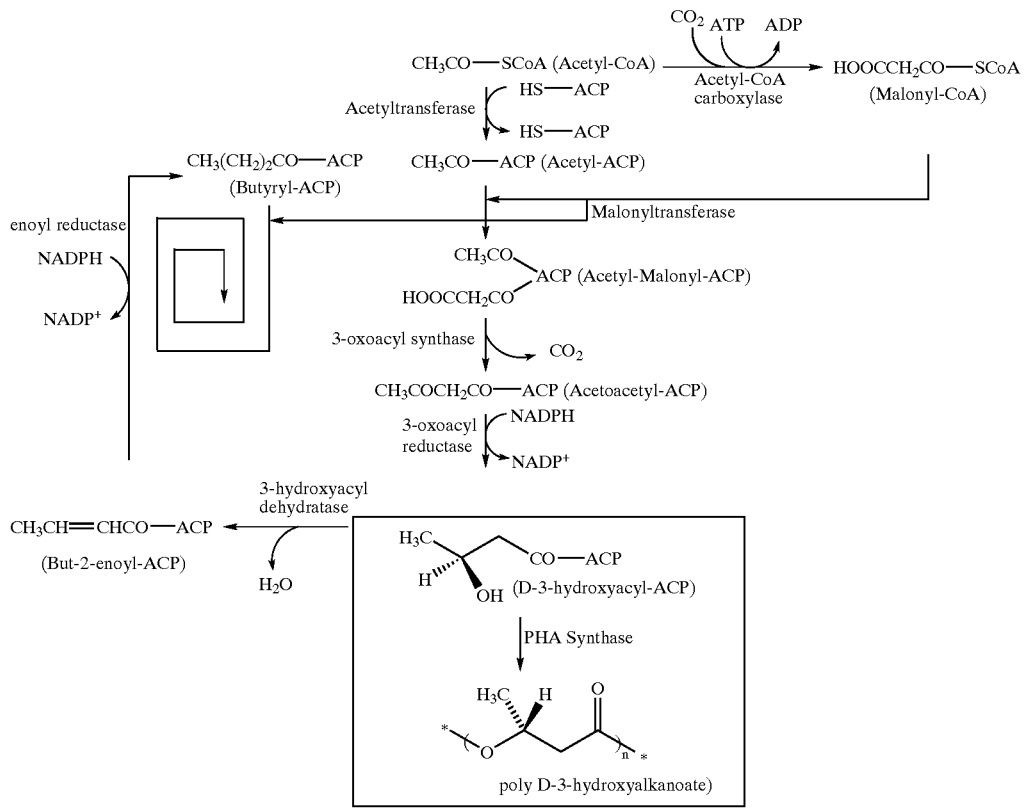

(2) Carbon chain expansion pathway

This pathway is classified broadly into two pathways, one of which is a pathway where malonyl-ACP is added to acyl-ACP to finally form acyl-ACP with the carbon chain extended by two (referred to as Pathway A) (and $CO_2$), and the other of which is a pathway where acetyl-CoA is added to acyl-CoA to finally form acyl-CoA with the carbon chain extended by two (referred to as Pathway B). Each pathway will be described below.

Pathway A

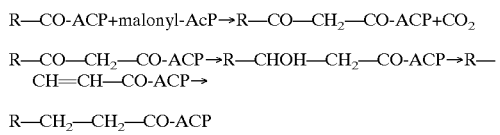

R—CH$_2$—CH$_2$—CO-ACP

Pathway B

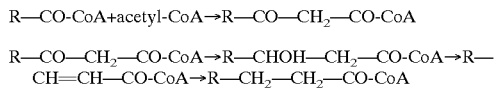

It can be considered that in both A and B systems, "D-3-hydroxyacyl-CoA" or "D-3-hydroxyacyl-ACP" is produced as an intermediate, and the "D-3-hydroxyacyl-CoA" is used directly as a monomer substrate for synthesis of PHA, and the "D-3-hydroxyacyl-ACP" is converted into "D-3-hydroxyacyl-CoA" by an ACP-CoA transferase and is then used as a monomer substrate for synthesis of PHA.

It can be considered that in the case of using saccharides such as glucose as a carbon source, mcl-3HA monomer unit are produced by way of the "glycolysis system" and the "fatty acid synthetic pathway" in the microorganism cells.

Here, it can be considered that mcl-alkanoic acids such as for example octanoic acid and nonanoic acid, or alkanoic acids with functional groups other than straight chain aliphatic alkyl added to the extremity such as for example 5-phenylvaleric acid, 4-phenoxybutyric acid, 4-cyclohexylbutyric acid and 5-(2-thienyl) valeric acid are changed into CoA derivatives by CoA ligase (EC 6.2.1.3 and so forth) and are directly changed into "D-3-hydroxyacyl-CoA" that is a monomer substrate for biosynthesis of PHA by an enzyme group responsible for β-oxidation systems.

Namely, while mcl-3HA monomer unit produced from saccharides are produced through extremely multi-staged enzyme reactions (i.e. indirectly), mcl-3HA monomer unit are produced extremely directly from mcl-alkanoic acid.

Now, production of acetyl-CoA responsible for growth of microorganisms will be described. In the method in which mcl-alkanoic acid is made to coexist in addition to alkanoic acid for incorporating desired monomer unit, these alkanoic acids go through the β-oxidation system, whereby acetyl-CoA is produced. Generally, it can be considered that the mcl-alkanoic acid has high affinity with an enzyme group of the β-oxidation system compared to alkanoic acids having bulky substituents (alkanoic acids having substituents such as phenyl groups, phenoxy groups, cyclohexyl groups and thienyl groups), and the acetyl-CoA is effectively produced by coexistence of the mcl-alkanoic acid. Therefore, it is advantageous for growth of microorganisms using the acetyl-CoA as energy sources and carbon sources.

However, the major problem is that produced PHA has large quantity of mcl-3HA monomer unit coexisting in addition to desired monomer unit because the mcl-alkanoic acid going through the β-oxidation system is directly changed into the monomer unit of PHA.

In order to solve this problem, a method in which a substance other than mcl-alkanoic acid capable of supplying effectively acetyl-CoA or energy sources and carbon sources is selected and is made to coexist with desired alkanoic acid is desirable. As described previously, the acetyl-CoA can become the monomer unit of PHA by going through the fatty acid synthetic pathway, but it is an indirect way where the acetyl-CoA needs to go through more multi-staged reactions compared to the mcl-alkanoic acid, and culture conditions such as the concentration of the substance enabling the production of acetyl-CoA are appropriately selected, thereby making it possible to achieve a producing method in which substantially, nor or little mcl-3HA coexists.

Also, producing methods in which culture is performed for the purpose of only growth of microorganisms in the first stage, and only desired alkanoic acid is added in the culture medium as carbon sources in the second stage are commonly used. At this time, according to the inventors and, due to the fact that the acyl-CoA ligase that is an initial fermentation enzyme of the β-oxidation system by which the alkanoic acid is made to be acyl-CoA requires ATP, the conclusion that a method in which a substance that can be used by microorganisms as an energy source also in the second stage is more effective has been reached, leading to the completion of the present invention.

For substances capable of supplying effectively acetyl-CoA or energy sources and carbon sources in the present invention, in addition to saccharides including aldoses such as gryceroaldehyde, erythrol, arabinose, xylose, glucose, galactose, mannose and fructose, algitol such as glycerol, erythritol and xylitol, aldonic acid such as gluconic acid, uronic acid such as glucronic acid and galacturonic acid, and disaccharides such as maltose, sucrose and lactose, any compounds including culture medium components derived from natural substances such as yeast extract, polypeptone, meat extract and casaminoic acid can be used as long as they are compounds capable of supplying acetyl-CoA or energy sources and carbon sources without going through the β-oxidation system, and they may be appropriately selected based on the usefulness as substances for strains to be used. Also, a plurality of compounds can be selected and used as long as the combination allows reduction of coexisting mcl-3HA.

Microorganisms

For microorganisms for use in the present invention, any microorganisms may be used, as long as they are capable of producing PHA containing as monomer unit the above described 3HTB, 3HTV, 3HTHx or 3HTHp, with the above described TVA, THxA or THpA as stocks. Also, a plurality of microorganisms may be mixed and used as necessary, within the scope where the object of the present invention can be achieved.

The present inventors performed screening of microorganisms capable of producing PHA containing as monomer unit the above described 3HTB, 3HTV and 3HTHx or 3HTHp using TVA, THxA or THpA as a stock. As a result, it has been found that Pseudomonas putida P91, *Pseudomonas cichorii* H45, *Pseudomonas cichorii* YN2 and *Pseudomonas jessenii* P161, which were microorganisms isolated from the soil by the present inventors, and are capable of producing PHA have the desired capability. Furthermore, the P91 strain, the H45 strain, the YN2 strain and P161 strain are deposited as "FERM BP-7373", "FERM BP-7374", "FERM BP-7375" and "FERM BP-7376", respectively in Patent Microorganism Deposition Center, Institute of Life Engineering Technology, Economic and Industrial Ministry whose address is 1-3, Higashi 1-chome, Tsukuba-shi, Ibaraki-ken, 305 Japan. Also, these microorganisms have been subjected to the international deposition based on Budapest Convention. The international accession numbers are as follows.

P91 strain: "FERM BP-7373", deposited Jun. 3, 1999
H45 strain: "FERM BP-7474", deposited Jun. 3, 1999
YN2 strain: "FERM BP-7375", deposited Jun. 3, 1999
P161 strain: "FERM BP-7376", deposited Jul. 1, 1999

Bacteriological properties of the above described P91 strain, H45 strain, YN2 strain and P161 strain are listed below. Also, as for the P161 strain, base sequence of 16S rRNA is shown in the arrangement number I.

Bacteriological Properties of P91 Strain
(1) Morphological Properties
Shape and size of cell: rod, 0.6 μm×1.5 μm
Polymorphism of cell: no polymorphism
Motility: motile
Sporulation: no sporulation
Gram staining: negative
Colony morphology: round, entirely smooth, low recess, smooth surface, glossy, creamy
(2) Physiological Properties
Catalase: positive
Oxidase: positive
O/F test: oxidation type
Reduction of nitrates: negative
Production of indole: negative
Glucose acidification: negative
Arginine dihydrolase: positive
Urease: negative
Esculin hydrolysis: negative
Gelatin hydrolysis: negative
β-galactosidase: negative
Fluorescent pigment production on King's B agar: positive
(3) Substrate Assimilability
Glucose: positive
L-arabinose: negative
D-mannose: negative
D-mannitol: negative
N-acetyl-D-gluconsamine: negative
Maltose: negative
Potassium gluconate: positive
n-capric acid: positive
Adipic acid: negative
d1-malic acid: positive
Sodium citrate: positive
Phenyl acetate: positive Bacteriological Properties of H45 Strain
(1) Morphological Properties
Shape and size of cell: rod, 0.8 μm×1.0 to 1.2 μm
Polymorphism of cell: no polymorphism
Motility: motile
Sporulation: no sporulation
Gram staining: negative
Colony morphology: round, entirely smooth, low recess, smooth surface, glossy, creamy
(2) Physiological Properties
Catalase: positive
Oxidase: positive
O/F test: oxidation type
Reduction of nitrates: negative
Production of indole: negative
Glucose acidification: negative
Arginine dihydrolase: negative Urease: negative
Esculin hydrolysis: negative
Gelatin hydrolysis: negative
β-galactosidase: negative
Fluorescent pigment production on King's B agar: positive
Growth in presence of 4% NaCl: negative
Accumulation of poly-β-hydroxybutyric acid: negative
(3) Substrate Assimilability
Glucose: positive
L-arabinose: negative
D-mannose: positive
D-mannitol: positive
N-acetyl-D-gluconsamine: positive
Maltose: negative
Potassium gluconate: positive
n-capric acid: positive
Adipic acid: negative
d1-malic acid: positive
Sodium citrate: positive
Phenyl acetate: positive Bacteriological Properties of YN2 Strain
(1) Morphological Properties
Shape and size of cell: rod, 0.8 μm×1.5 to 2.0 μm
Polymorphism of cell: no polymorphism
Motility: motile
Sporulation: no sporulation
Gram staining: negative
Colony morphology: round, entirely smooth, low recess, smooth surface, glossy, translucent
(2) Physiological Properties
Catalase: positive
Oxidase: positive
O/F test: oxidation type
Reduction of nitrates: negative
Production of indole: positive
Glucose acidification: negative
Arginine dihydrolase: negative
Urease: negative
Esculin hydrolysis: negative
Gelatin hydrolysis: negative
β-galactosidase: negative
Fluorescent pigment production on King's B agar: positive
Growth in presence of 4% NaCl: positive (weak growth)
Accumulation of poly-β-hydroxybutyric acid: negative
Hydrolysis of Tween 80: positive
(3) Substrate Assimilability
Glucose: positive
L-arabinose: positive
D-mannose: negative
D-mannitol: negative
N-acetyl-D-gluconsamine: negative
Maltose: negative
Potassium gluconate: positive
n-capric acid: positive
Adipic acid: negative
d1-malic acid: positive
Sodium citrate: positive
Phenyl acetate: positive Bacteriological Properties of P161 Strain
(1) Morphological Properties
Shape and size of cell: sphere, φ0.6 μrod, 0.6 μm×1.5 to 2.0 μm
Polymorphism of cell: shown (expansion type)
Motility: motile
Sporulation: no
Gram staining: negative
Colony morphology: round, entirely smooth, low recess, smooth surface, light yellow
(2) Physiological Properties
Catalase: positive
Oxidase: positive
O/F test: oxidation type
Reduction of nitrates: positive
Production of indole: negative
Glucose acidification: negative
Arginine dihydrolase: positive
Urease: negative
Esculin hydrolysis: negative
Gelatin hydrolysis: negative
β-galactosidase: negative
Fluorescent pigment production on King's B agar: positive
(3) Substrate Assimilability
Glucose: positive
L-arabinose: positive
D-mannose: positive
D-mannitol: positive
N-acetyl-D-gluconsamine: positive
Maltose: negative
Potassium gluconate: positive
n-capric acid: positive
Adipic acid: negative
d1-malic acid: positive
Sodium citrate: positive
Phenyl acetate: positive Culture Desired PHA can be produced by culturing these microorganisms on a culture medium containing alkanoate for incorporating desired monomer unit and carbon sources for growth of the present invention. This PHA is composed of only R-bodies and is an isotactic polymer.

For normal culture of microorganisms for use in the method of PHA related to the present invention, for example for preparation of stocked strains and growth for securing the number of strains and active conditions required for production of PHA, a culture medium containing components necessary for growth of microorganisms to be used is appropriately selected and used. For example, any kinds of culture mediums may be used such as general natural culture mediums (nutrient broth, yeast extract, etc.) and synthetic culture mediums to which nutrient sources are added, as long as they do not adversely affect the growth and survival of microorganisms.

For culture, any culture processes such as liquid culture and solid culture may be used as long as they are culture processes through which microorganisms are grown and PHA is produced. Furthermore, there are also no limitations on types of culture including batch culture, fed batch culture, semi-continuous culture and continuous culture. Forms of liquid batch culture include methods in which oxygen is supplied through shaking by a shaking flask, and oxygen supplying methods of stirring and aeration systems using jar fermenters. Multiple-stage systems connecting two or more of these processes may be adopted.

In the case where PHA containing 3HTB, 3HTV, 3HTHx or 3HTHp as monomer unit is produced using PHA production microorganisms as described above, inorganic culture mediums and the like containing at least each corresponding TVA, THXA and THpA as stocks for production of PHA and carbon sources for growth may be used. As carbon sources for growth, nutrients such as yeast extract, polypeptone and meat extract can be used, and furthermore any compounds including saccharides, for example aldoses such as gryceroaldehyde, erythrol, arabinose, xylose, glucose, galactose, mannose and fructose, algitol such as glycerol, erythritol and xylitol, aldonic acid such as gluconic acid, uronic acid such as glucronic acid and galacturonic acid, and disaccharides such as maltose, sucrose and lactose can be used, as long as they are compounds producing acetyl-CoA without going through the β-oxidation cycle, and they may be appropriately selected based on the usefulness as carbon source for strains to be used. Also, a plurality of compounds can be selected and used as long as the combination allows reduction of coexisting mcl-3HA. Among these, saccharides are particularly preferably used, and more preferably is one selected from a group constituted by glucose, fructose and mannose. For methods of making microorganisms produce and accumulate PHA, after microorganisms are sufficiently grown, the cell is transferred to the culture medium where nitrogen sources such as ammonium chloride are limited, and culture is further performed with compounds that are raw materials of desired units being added, whereby productivity may be improved. Specifically, a multiple-stage system connecting two or more of the above described processes is adopted. For example, there is a method in which culture is performed on an inorganic culture medium, etc. containing about 0.05% to 5.0% of D-glucose and about 0.01% to 1.0% of TVA, THxA or THpA until the point of the logarithmic growth phase or the stationary phase, and the cell is collected by centrifugation and the like, followed by performing culture on the inorganic culture medium containing about 0.01% to 1.0% of TVA, THxA or THpA where nitrogen sources are limited or substantially no nitrogen sources exist.

Inorganic culture mediums for use in the aforesaid culture methods may be any mediums as long as they contain components allowing microorganisms to grow, such as phosphorus sources (e.g. phosphate) and nitrogen sources (e.g. ammonium salts and nitrate), and culture mediums of inorganic salts may include, for example, MSB culture mediums, E culture mediums (J. Biol. Chem. 218, 97–106 (1956)), M9 culture mediums and the like.

Furthermore, the composition of the M9 culture medium used for Example in the present invention is as follows.

$Na_2HPO_4$: 6.2 g
$KH_2PO_4$: 3.0 g
NaCl: 0.5 g
$NH_4Cl$: 1.0 g
(per liter of culture medium, pH 7.0)

Furthermore, for favorable growth and production of PHA, it is preferable that about 0.3% (v/v) of micro component solutions described below are added in the above described inorganic culture mediums.

Micro component solutions
Nitrilo triacetic acid: 1.5 g
$MgSO_4$: 3.0 g
$MnSO_4$: 0.5 g
NaCl: 1.0 g
$FeSO_4$: 0.1 g
$CaCl_2$: 0.1 g
$CoCl_2$: 0.1 g
$ZnSO_4$: 0.1 g
$CUSO_4$: 0.1 g
$AlK(SO_4)_2$: 0.1 g
$H_3BO_3$: 0.1 g
$Na_2MoO_4$: 0.1 g
$NiCl_2$: 0.1 g
(per liter)

Culture temperature may be temperature allowing the above described strains to grow favorably, and suitable is for example 14 to 40° C., preferably about 20 to 35° C.

For a specific example, culture is performed on an inorganic culture medium, etc. containing about 0.05% to 5.0% of D-glucose and about 0.01% to 1.0% of TVA, THxA or THpA, and the cell is collected at the point of the logarithmic growth phase or the stationary phase, whereby desired PHA having little or no undesired monomer unit coexisting can be extracted. This PHA is generally composed of only R-bodies, and is an isotactic polymer.

The same amount of yeast extract or polypeptone may also be given in place of D-glucose. Also, combinations thereof may be used.

Collection of PHA

Methods that are usually performed may be applied for collection of PHA from culture solution related to the present invention. An method of extractive purification from the culture solution is used in the case where PHA is secreted in the culture solution, and a method of extractive purification from the cell in the case where PHA is accumulated in the cell. For example, for collecting PHA from the cultured cell of microorganisms, extraction using organic solvents such as chloroform as usually performed is simplest, but there may be cases where acetone is used in place of chloroform. Also, in environments where it is difficult to use organic solvents, methods in which cell components other than PHA are removed through processes using surfactants such as SDS, processes using enzymes such as lysozyme and processes using chemicals such as EDTA, sodium hypochloride and ammonia to collect PHA may be used.

Furthermore, culture of microorganisms of the present invention, production of PHA by microorganisms and accumulation in the cell according to the present invention, and collection of PHA from the cell in the present invention should not be limited to the above described methods.

Examples are shown below. Furthermore, "%" in the following is based on weight unless specifically stated.

EXAMPLES

Example 1

*Pseudomonas putida* P91 was inoculated into 200 ml of M9 culture medium containing 0.5% of yeast extract (manufactured by Difco) and 0.1% of TVA, and was subjected to shaking culture at 125 strokes/minute at 30° C. After 24 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit.

Consequently, as a shown in Table 1, such PHA was identified as PHA having only 3HTV as a monomer unit.

TABLE 1

Production of PHA by *Pseudomonas putida* P91

| | |
|---|---|
| Dry weight of cell | 590 mg/L |
| Dry weight of polymer | 7 mg/L |
| Dry weight of polymer/Dry weight of cell | 1% |
| Composition of monomer unit ((GC-MS, TIC peak area ratio) | |
| 3-hydroxy-5-(2-thienyl) valeric acid | 100% |

With respect to this PHA, analysis was carried out under the following measurement condition, using nuclear magnetic resonance equipment (FT•NMR: Bruker DPX 400).

Figure 2:
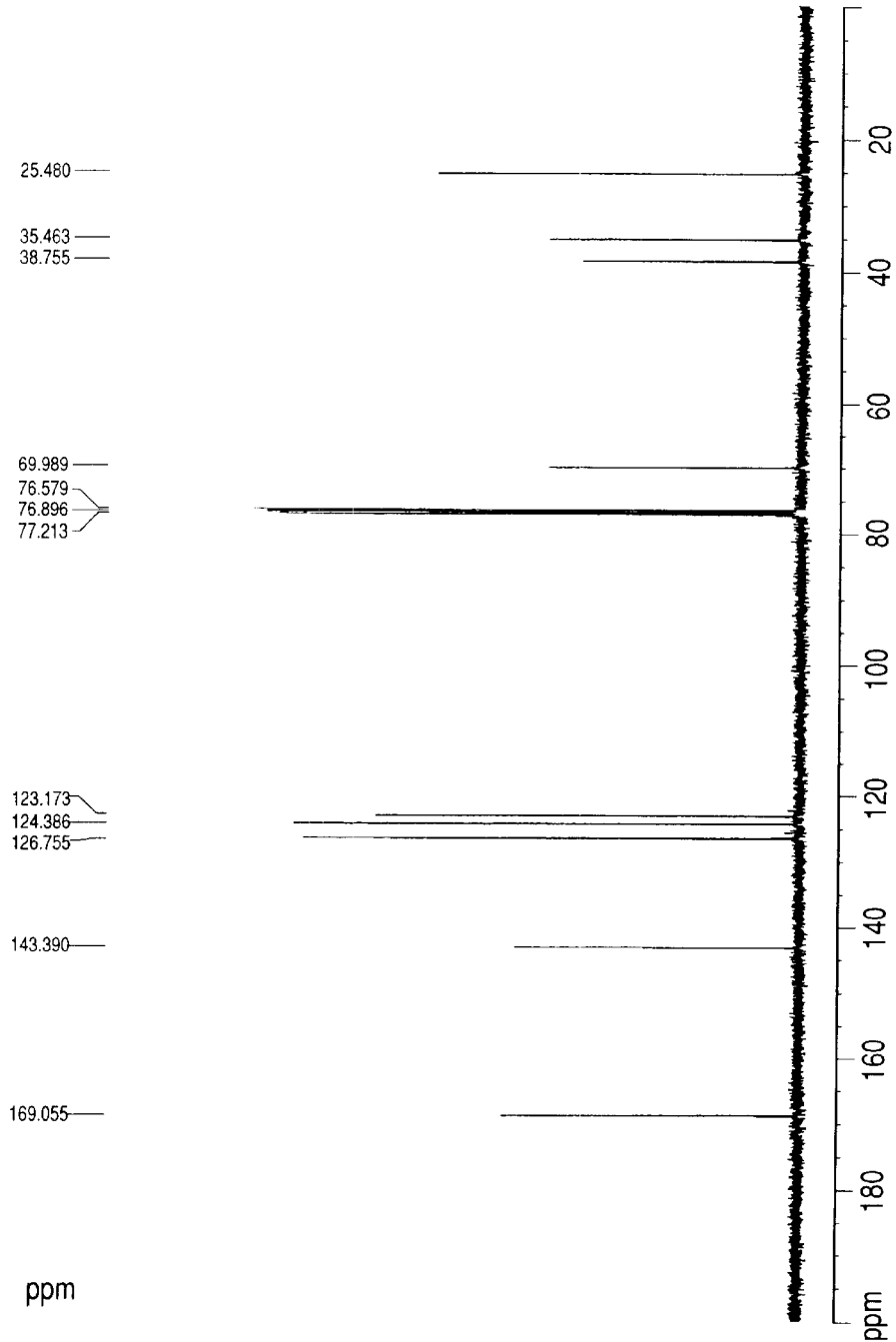
FIG. 2 illustrates a $^{13}$C-NMR spectrum of a polymer using TVA as a raw material in Example 1.

Measurement Condition
Measurement nuclide: $^1H$, $^{13}C$
Solvent used: $CDCl_3$ (TMS/$CDCl_3$ included in a capillary was used as a reference.)
Resonance frequencies: $^1H$=400 MHz, $^{13}C$=100 MHz $^1H$ and $^{13}C$-NMR spectra, and results of assignment thereof (see Chemical Formula [14]) are shown in FIGS. 1 and 2, and Table 2, respectively.

TABLE 2

[14]

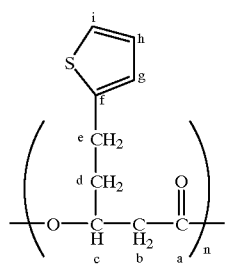

Results of assignment of $^1H$ and $^{13}C$-NMR spectra

| | 1H | | | 13C |
|---|---|---|---|---|
| Position | Chemical shift/ ppm | Integral value | Type | Chemical shift /ppm |
| a | — | — | — | 169.1 |
| b | 2.52 | 2 | m | 35.5 |
| c | 5.23 | 1 | m | 70.0 |
| d | 1.97 | 2 | m | 35.5 |
| e | 2.82 | 2 | m | 25.5 |
| f | — | — | — | 143.4 |
| g | 6.76 | 1 | dd | 124.4 |
| h | 6.87 | 1 | dd | 126.8 |
| i | 7.07 | 1 | d | 123.2 | d: doulet,
dd: double doublet,
t: triplet,
m: multiplet

Furthermore, the result of evaluating the molecular weight of this PHA with gel permeation chromatography (GPC; Tosoh HL C-8020, Column; Polymer Laboratory PL gel MIXED-C (5 μm), Solvent; chloroform, polystyrene conversion) was Mn=72,000, Mw=260,000.

Example 2

*Pseudomonas cichorii* YN2 was inoculated into 200 ml of M9 culture medium containing 0.5% of D-glucose and 0.1% of TVA, and was subjected to shaking culture at 125 strokes/minute at 30° C. After 48 hours, the cell was collected by centrifugation, and was suspended again in 200 ml of M9 culture medium containing 0.5% of D-glucose and 0.1% of TVA, and no nitrate source ($NH_4Cl$), and was further subjected to shaking culture at 125 strokes/minute at 30° C. After 42 hours, the cell was collected through centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 3, such PHA was identified as PHA having monomer unit represented by the above described Chemical Formula [6].

TABLE 3

Production of PHA by *Pseudomonas cichorii* YN2

| | |
|---|---|
| Dry weight of cell | 1300 mg/L |
| Dry weight of polymer | 820 mg/L |
| Dry weight of polymer/Dry weight of cell | 63% |
| Composition of monomer unit ((GC-MS, TIC peak area ratio) | |
| 3-hydroxyoctanoic acid | 1% |
| 3-hydroxydecanoic acid | 1% |
| 3-hydroxydodecanoic acid | 1% |
| 3-hydroxy-5-(2-thienyl) valeric acid | 97% |

Example 3

*Pseudomonas cichorii* H45 was inoculated into 200 ml of M9 culture medium containing 0.5% of D-glucose and 0.1% of TVA, and was subjected to shaking culture at 125 strokes/minute at 30° C. After 48 hours, the cell was collected by centrifugation, and was suspended again in 200 ml of M9 culture medium containing 0.5% of D-glucose and 0.1% of TVA, and no nitrate source ($NH_4Cl$), and was further subjected to shaking culture at 125 strokes/minute at 30° C. After 42 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 4, such PHA was identified as PHA having monomer unit represented by the above described Chemical Formula [6].

TABLE 4

| Production of PHA by *Pseudomonas cichorii* H45 | |
|---|---|
| Dry weight of cell | 660 mg/L |
| Dry weight of polymer | 270 mg/L |
| Dry weight of polymer/Dry weight of cell | 41% |
| Composition of monomer unit ((GC-MS, TIC peak area ratio) | |
| 3-hydroxyoctanoic acid | 1% |
| 3-hydroxy-5-(2-thienyl) valeric acid | 99% |

Example 4

*Pseudomonas jessenii* P161 was inoculated into 200 ml of M9 culture medium containing 0.5% of D-glucose and 0.1% of TVA, and was subjected to shaking culture at 125 strokes/minute at 30° C. After 46 hours, the cell was collected by centrifugation, and was suspended again in 200 ml of M9 culture medium containing 0.5% of D-glucose and 0.1% of TVA, and no nitrate source ($NH_4Cl$), and was further subjected to shaking culture at 125 strokes/minute at 30° C. After 41 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 5, such PHA was identified as PHA having monomer unit represented by the above described Chemical Formula [6].

TABLE 5

| Production of PHA by *Pseudomonas jessenii* P161 | |
|---|---|
| Dry weight of cell | 820 mg/L |
| Dry weight of polymer | 480 mg/L |
| Dry weight of polymer/Dry weight of cell | 59% |
| Composition of monomer unit ((GC-MS, TIC peak area ratio) | |
| 3-hydroxyoctanoic acid | 1% |
| 3-hydroxydecanoic acid | 1% |
| 3-hydroxy-5-(2-thienyl) valeric acid | 98% |

Example 5

*Pseudomonas cichorii* YN2 was inoculated into 200 ml of M9 culture medium containing 0.5% of polypeptone (manufactured by Nihon Seiyaku) and 0.1% of THxA, and was subjected to shaking culture at 125 strokes/minute at 30° C. After 48 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 6, such PHA was identified as PHA having monomer unit represented by the above described Chemical Formula [8].

TABLE 6

| Production of PHA by *Pseudomonas cichorii* YN2 | |
|---|---|
| Dry weight of cell | 620 mg/L |
| Dry weight of polymer | 300 mg/L |
| Dry weight of polymer/Dry weight of cell | 48% |
| Composition of monomer unit ((GC-MS, TIC peak area ratio) | |
| 3-hydroxybutyric acid | 16% |
| 3-hydroxy-4-(2-thienyl) butyric acid | 4% |
| 3-hydroxy-6-(2-thienyl) hexanoic acid | 80% |

With respect to these PHA, analysis was carried out under the following measurement condition, using nuclear magnetic resonance equipment (FT-NMR: Bruker DPX 400).

Figure 3:
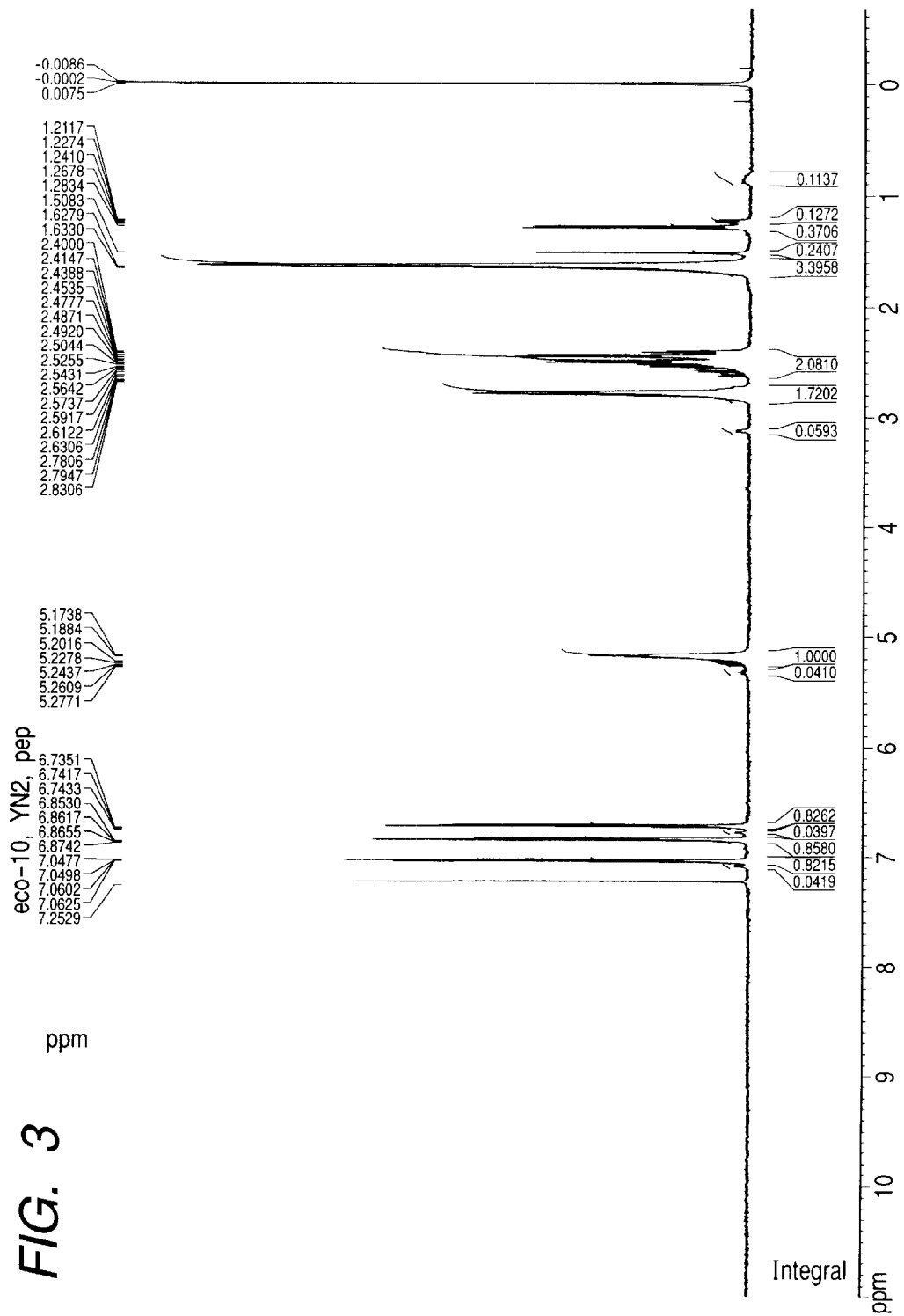
FIG. 3 illustrates a $^1$H-NMR spectrum of a polymer using THxA as a raw material in Example 5.

Measurement Condition
Measurement nuclide: $^1H$
Solvent used: $CDCl_3$ ($TMS/CDC_3$ included in a capillary was used as a reference.)
Resonance frequencies: $^1H$=400 MHz The $^1H$-NMR spectrum, and results of assignment thereof (see Chemical Formulae: 3-hydroxy-4-(2-thienyl) butyric acid [15], 3-hydroxy-6-(2-thienyl) hexanoic acid [16], and 3-hydroxybutyric acid [17]) are shown in FIG. 3 and Table 7, respectively.

TABLE 7

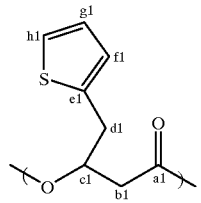

[15]

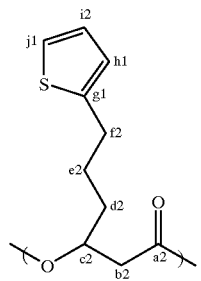

[16]

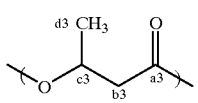

[17]

| Chemical shift (ppm) | Integral value | Type | Result of identification |
|---|---|---|---|
| 1.27 | 0.41 | d | d3 |
| 1.63 | 3.95 | m | d2, e2 |
| 2.40–2.63 | 2.43 | m | b1, b2, b3 |
| 2.79 | 1.99 | m | f2 |
| 3.12 | 0.06 | m | d1 |
| 5.17–5.27 | 1.15 | m | c2, c3 |
| 5.33 | 0.04 | m | c1 |
| 6.74 | 0.82 | dd | h2 |
| 6.80 | 0.04 | m | f2 |
| 6.86 | 0.86 | quart | g1, i2 |
| 7.05 | 0.82 | dd | j2 |
| 7.10 | 0.04 | dd | h1 | d: doublet,
dd: double doublet,
t: triplet, quart: quartct,
m: multiplet

Furthermore, the result of evaluating the molecular weight of this PHA with gel permeation chromatography (GPC; Tosohh HL C-8020, Column; Polymer Laboratory PL gel MIXED-C (5 μm), Solvent; chloroform, polystyrene conversion) was Mn=180,000, Mw=411,000.

Example 6

Pseudomonas jessenii P161 was inoculated into 200 ml of M9 culture medium containing 0.5% of polypeptone (manufactured by Nihon Seiyaku) and 0.1% of THxA, and was subjected to shaking culture at 125 strokes/minute at 30° C. After 48 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 8, such PHA was identified as PHA having monomer unit represented by the above described Chemical Formula [8].

TABLE 8

Production of PHA by *Pseudomonas jessenii* P161

| | |
|---|---|
| Dry weight of cell | 390 mg/L |
| Dry weight of polymer | 170 mg/L |
| Dry weight of polymer/Dry weight of cell | 44% |

| Composition of monomer unit (GC-MS, TIC peak area ratio) | |
|---|---|
| 3-hydroxy-4-(2-thienyl) butyric acid | 4% |
| 3-hydroxy-6-(2-thienyl) hexanoic acid | 96% |

Example 7

Pseudomonas cichorii H45 was inoculated into 200 ml of M9 culture medium containing 0.5% of polypeptone (manufactured by Nihon Seiyaku) and 0.1% of THxA, and was subjected to shaking culture at 125 strokes/minute at 30° C. After 48 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 9, such PHA was identified as PHA having monomer unit represented by the above described Chemical Formula [8].

TABLE 9

Production of PHA by *Pseudomonas cichorii* H45

| | |
|---|---|
| Dry weight of cell | 350 mg/L |
| Dry weight of polymer | 140 mg/L |
| Dry weight of polymer/Dry weight of cell | 40% |

| Composition of monomer unit (GC-MS, TIC peak area ratio) | |
|---|---|
| 3-hydroxybutyric acid | 1% |
| 3-hydroxy-4-(2-thienyl) butyric acid | 5% |
| 3-hydroxy-6-(2-thienyl) hexanoic acid | 94% |

Example 8

Pseudomonas cichorii YN2 was inoculated into 200 ml of M9 culture medium containing 0.5% of D-glucose and 0.1% of THxA, and was subjected to shaking culture at 125 strokes/minute at 30° C. After 48 hours, the cell was collected by centrifugation, and was suspended again in 200 ml of M9 culture medium containing 0.5% of D-glucose and 0.1% of THxA, and no nitrate source ($NH_4Cl$), and was further subjected to shaking culture at 125 strokes/minute at 30° C. After 42 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 10, such PHA was identified as PHA having monomer unit represented by the above described Chemical Formula [8].

TABLE 10

Production of PHA by *Pseudomonas cichorii* YN2

| | |
|---|---|
| Dry weight of cell | 1280 mg/L |
| Dry weight of polymer | 660 mg/L |
| Dry weight of polymer/Dry weight of cell | 52% |

Composition of monomer unit (GC-MS, TIC peak area ratio)

| | |
|---|---|
| 3-hydroxybutyric acid | 2% |
| 3-hydroxyhexanoic acid | 1% |
| 3-hydroxyoctanoic acid | 7% |
| 3-hydroxydecanoic acid | 14% |
| 3-hydroxydodecanoic acid | 5% |
| 3-hydroxytetradecanoic acid | 8% |
| 3-hydroxy-4-(2-thienyl) butyric acid | 2% |
| 3-hydroxy-6-(2-thienyl) hexanoic acid | 61% |

Example 9

*Pseudomonas jessenii* P161 was inoculated into 200 ml of M9 culture medium containing 0.5% of D-glucose and 0.1% of THxA, and was subjected to shaking culture at 125 strokes/minute at 30° C. After 48 hours, the cell was collected by centrifugation, and was suspended again in 200 ml of M9 culture medium containing 0.5% of D-glucose and 0.1% of THxA, and no nitrate source ($NH_4Cl$), and was further subjected to shaking culture at 125 strokes/minute at 30° C. After 42 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 $\mu$m, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 11, such PHA was identified as PHA having monomer unit represented by the above described Chemical Formula [8].

TABLE 11

Production of PHA by *Pseudomonas jessenii* P161

| | |
|---|---|
| Dry weight of cell | 1080 mg/L |
| Dry weight of polymer | 534 mg/L |
| Dry weight of polymer/Dry weight of cell | 49% |

Composition of monomer unit (GC-MS, TIC peak area ratio)

| | |
|---|---|
| 3-hydroxybutyric acid | 1% |
| 3-hydroxyhexanoic acid | 1% |
| 3-hydroxyoctanoic acid | 5% |
| 3-hydroxydecanoic acid | 6% |
| 3-hydroxydodecanoic acid | 2% |
| 3-hydroxytetradecanoic acid | 3% |
| 3-hydroxy-4-(2-thienyl) butyric acid | 3% |
| 3-hydroxy-6-(2-thienyl) hexanoic acid | 79% |

Example 10

*Pseudomonas cichorii* H45 was inoculated into 200 ml of M9 culture medium containing 0.5% of D-glucose and 0.1% of THxA, and was subjected to shaking culture at 125 strokes/minute at 30° C. After 48 hours, the cell was collected by centrifugation, and was suspended again in 200 ml of M9 culture medium containing 0.5% of D-glucose and 0.1% of THxA, and no nitrate source ($NH_4Cl$), and was further subjected to shaking culture at 125 strokes/minute at 30° C. After 42 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 $\mu$m, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 12, such PHA was identified as PHA having monomer unit represented by the above described Chemical Formula [8].

TABLE 12

Production of PHA by *Pseudomonas cichorii* H45

| | |
|---|---|
| Dry weight of cell | 1150 mg/L |
| Dry weight of polymer | 620 mg/L |
| Dry weight of polymer/Dry weight of cell | 54% |

Composition of monomer unit (GC-MS, TIC peak area ratio)

| | |
|---|---|
| 3-hydroxyoctanoic acid | 4% |
| 3-hydroxydecanoic acid | 6% |
| 3-hydroxydodecanoic acid | 2% |
| 3-hydroxytetradecanoic acid | 3% |
| 3-hydroxy-4-(2-thienyl) butyric acid | 3% |
| 3-hydroxy-6-(2-thienyl) hexanoic acid | 82% |

Example 11

*Pseudomonas cichorii* YN2 was inoculated into 200 ml of M9 culture medium containing 0.5% of polypeptone (manufactured by Nihon Seiyaku) and 0.1% of THpA, and was subjected to shaking culture at 125 strokes/minute at 30° C. After 48 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 $\mu$m, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 13, such PHA was identified as PHA having monomer unit represented by the above described Chemical Formula [9].

TABLE 13

Production of PHA by *Pseudomonas cichorii* YN2

| | |
|---|---|
| Dry weight of cell | 590 mg/L |
| Dry weight of polymer | 220 mg/L |
| Dry weight of polymer/Dry weight of cell | 37% |
| Composition of monomer unit (GC-MS, TIC peak area ratio) | |
| 3-hydroxy-5-(2-thienyl) valeric acid | 82% |
| 3-hydroxy-7-(2-thienyl) heptanoic acid | 18% |

With respect to these PHA, analysis was carried out under the following measurement condition, using nuclear magnetic resonance equipment (FT-NMR: Bruker DPX 400).

Figure 4:
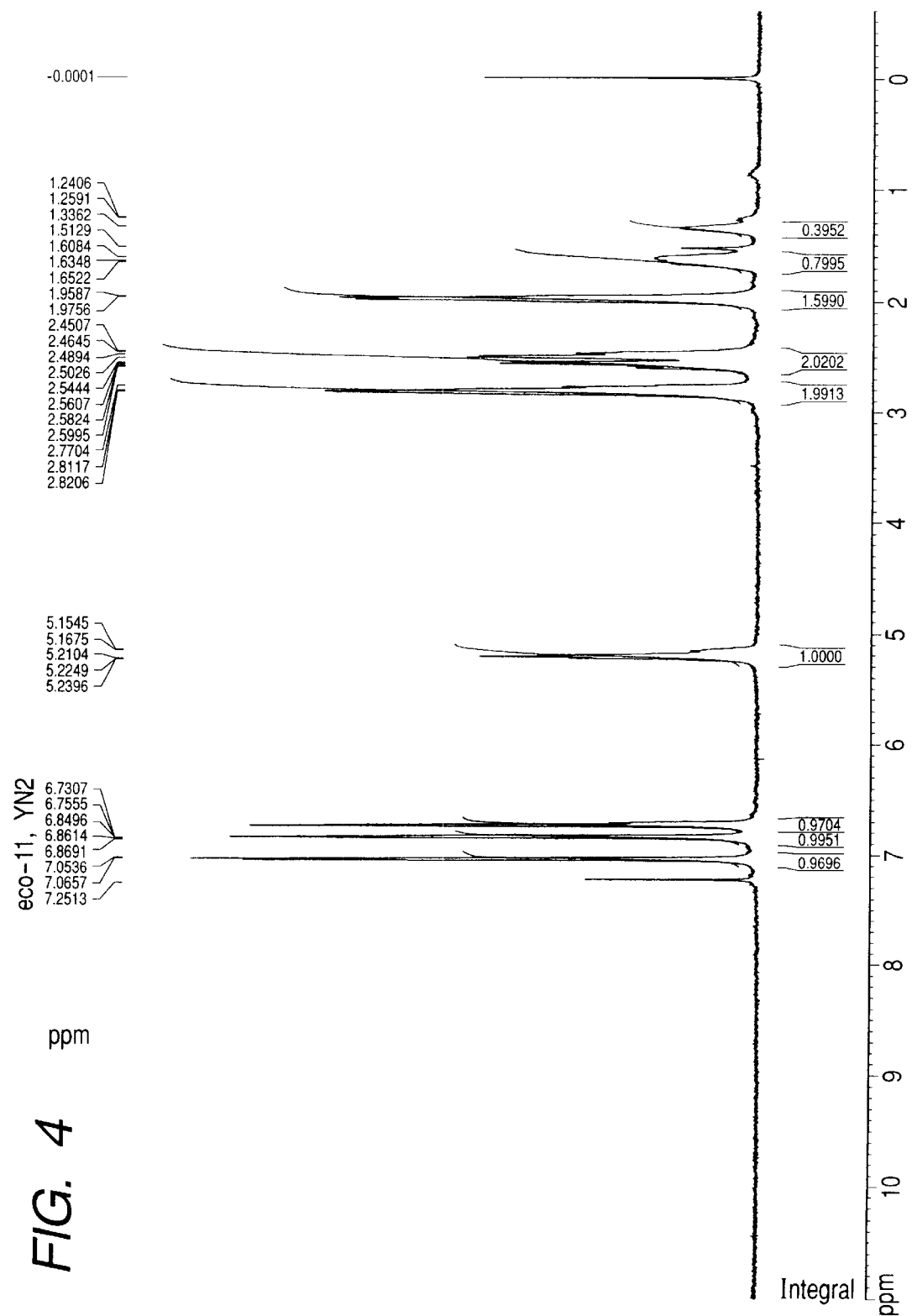
FIG. 4 illustrates a $^1$H-NMR spectrum of a polymer using THPA as a raw material in Example 11.

Measurement Condition
Measurement nuclide: $^1H$
Solvent used: $CDCl_3$ ($TMS/CDCl_3$ included in a capillary was used as a reference.)
Resonance frequencies: $^1H$=400 MHz The $^1$H-NMR spectrum, and results of assignment thereof (see Chemical Formulae: 3-hydroxy-5-(2-thienyl) valeric acid [18] and 3-hydroxy-7-(2-thienyl) heptanoic acid [19]) are shown in FIG. 4 and Table 14, respectively.

TABLE 14

[18]

[19]

| Chemical shift (ppm) | Integral value | Type | Result of identification |
|---|---|---|---|
| 1.33 | 0.40 | m | e2 |
| 1.64 | 0.80 | m | d2, f2 |
| 1.96 | 1.60 | m | d1 |
| 2.45–2.59 | 2.02 | m | b1, b1 |
| 2.77–2.82 | 1.99 | m | e1, g2 |
| 5.15–5.24 | 1.00 | m | c1, c2 |
| 6.74 | 0.97 | d | g1, i2 |
| 6.86 | 1.00 | t | h1, j2 |
| 7.06 | 0.97 | d | i1, k2 | d: doublet,
t: triplet,
m: multiplet

Furthermore, the result of evaluating the molecular weight of this PHA with gel permeation chromatography (GPC; Tosoh HL C-8020, Column; Polymer Laboratory PL gel MIXED-C (5 μm), Solvent; chloroform, polystyrene conversion) was Mn=49,000, Mw=88,000.

Example 12

*Pseudomonas jessenii* P161 was inoculated into 200 ml of M9 culture medium containing 0.5% of polypeptone (manufactured by Nihon Seiyaku) and 0.1% of THpA, and was subjected to shaking culture at 125 strokes/minute at 30° C. After 48 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 15, such PHA was identified as PHA having monomer unit represented by the above described Chemical Formula [9].

TABLE 15

Production of PHA by *Pseudomonas jessenii* P161

| | |
|---|---|
| Dry weight of cell | 970 mg/L |
| Dry weight of polymer | 550 mg/L |
| Dry weight of polymer/Dry weight of cell | 56% |
| Composition of monomer unit (GC-MS, TIC peak area ratio) | |
| 3-hydroxybutylic acid | 4% |
| 3-hydroxy-5-(2-thienyl) valeric acid | 61% |
| 3-hydroxy-7-(2-thienyl) heptanoic acid | 36% |

Example 13

*Pseudomonas cichorii* H45 was inoculated into 200 ml of M9 culture medium containing 0.5% of polypeptone (manufactured by Nihon Seiyaku) and 0.1% of THpA, and was subjected to shaking culture at 125 strokes/minute at 30° C. After 48 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 μm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 16, such PHA was identified as PHA having monomer unit represented by the above described Chemical Formula [9].

TABLE 16

Production of PHA by *Pseudomonas cichorii* H45

| | |
|---|---|
| Dry weight of cell | 450 mg/L |
| Dry weight of polymer | 200 mg/L |
| Dry weight of polymer/Dry weight of cell | 44% |
| Composition of monomer unit (GC-MS, TIC peak area ratio) | |
| 3-hydroxy-5-(2-thienyl) valeric acid | 68% |
| 3-hydroxy-7-(2-thienyl) heptanoic acid | 32% |

Example 14

*Pseudomonas cichorii* YN2 was inoculated into 200 ml of M9 culture medium containing 0.5% of D-glucose and 0.1% of THpA, and was subjected to shaking culture at 125 strokes/minute at 30° C. After 48 hours, the cell was collected by centrifugation, and was suspended again in 200 ml of M9 culture medium containing 0.5% of D-glucose and 0.1% of THpA, and no nitrate source ($NH_4Cl$), and was further subjected to shaking culture at 125 strokes/minute at 30° C. After 43 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 µm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 17, such PHA was identified as PHA having monomer unit represented by the above described Chemical Formula [9].

TABLE 17

Production of PHA by *Pseudomonas cichorii* YN2

| | |
|---|---|
| Dry weight of cell | 1540 mg/L |
| Dry weight of polymer | 1090 mg/L |
| Dry weight of polymer/Dry weight of cell | 71% |
| Composition of monomer unit (GC-MS, TIC peak area ratio) | |
| 3-hydroxybutyric acid | 1% |
| 3-hydroxyhexanoic acid | 1% |
| 3-hydroxyoctanoic acid | 3% |
| 3-hydroxydecanoic acid | 6% |
| 3-hydroxydodecanoic acid | 3% |
| 3-hydroxytetradecanoic acid | 5% |
| 3-hydroxy-5-(2-thienyl) valeric acid | 58% |
| 3-hydroxy-7-(2-thienyl) heptanoic acid | 23% |

Example 15

*Pseudomonas jessenii* P161 was inoculated into 200 ml of M9 culture medium containing 0.5% of D-glucose and 0.1% of THpA, and was subjected to shaking culture at 125 strokes/minute at 30° C. After 48 hours, the cell was collected by centrifugation, and was suspended again in 200 ml of M9 culture medium containing 0.5% of D-glucose and 0.1% of THpA, and no nitrate source ($NH_4Cl$), and was further subjected to shaking culture at 125 strokes/minute at 30° C. After 42 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 µm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 18, such PHA was identified as PHA having monomer unit represented by the above described Chemical Formula [9].

TABLE 18

Production of PHA by *Pseudomonas jessenii* P161

| | |
|---|---|
| Dry weight of cell | 1180 mg/L |
| Dry weight of polymer | 736 mg/L |
| Dry weight of polymer/Dry weight of cell | 62% |
| Composition of monomer unit (GC-MS, TIC peak area ratio) | |
| 3-hydroxybutyric acid | 1% |
| 3-hydroxyoctanoic acid | 2% |
| 3-hydroxydecanoic acid | 2% |
| 3-hydroxydodecanoic acid | 1% |
| 3-hydroxytetradecanoic acid | 2% |
| 3-hydroxy-5-(2-thienyl) valeric acid | 62% |
| 3-hydroxy-7-(2-thienyl) heptanoic acid | 30% |

Example 16

*Pseudomonas cichorii* H45 was inoculated into 200 ml of M9 culture medium containing 0.5% of D-glucose and 0.1% of THPA, and was subjected to shaking culture at 125 strokes/minute at 30° C. After 48 hours, the cell was collected by centrifugation, and was suspended again in 200 ml of M9 culture medium containing 0.5% of D-glucose and 0.1% of THpA, and no nitrate source ($NH_4Cl$), and was further subjected to shaking culture at 125 strokes/minute at 30° C. After 43 hours, the cell was collected by centrifugation, and was once washed with cold methanol and freeze-dried.

This freeze-dried pellet was suspended in 20 ml of chloroform, and was stirred at 60° C. for 20 hours to extract PHA. After the extracted solution was filtered through a membrane filter with the pore size of 0.45 µm, it was concentrated with a rotary evaporator, the concentrated solution was precipitated again in cold methanol, and only precipitate was collected and were subjected to vacuum drying to obtain PHA.

The obtained PHA was subjected to methanolysis according to the conventional method, and was then analyzed with a gas chromatography-mass spectrometer (GC-MS, Shimadzu QP-5050, EI mode) to perform identification of methyl esterified substances of PHA monomer unit. Consequently, as shown in Table 19, such PHA was identified as PHA having monomer unit represented by the above described Chemical Formula [9].

TABLE 19

Production of PHA by *Pseudomonas cichorii* H45

| | |
|---|---|
| Dry weight of cell | 1240 mg/L |
| Dry weight of polymer | 851 mg/L |
| Dry weight of polymer/Dry weight of cell | 69% |
| Composition of monomer unit (GC-MS, TIC peak area ratio) | |
| 3-hydroxybutyric acid | 1% |

TABLE 19-continued

| | |
|---|---|
| 3-hydroxyoctanoic acid | 2% |
| 3-hydroxydecanoic acid | 2% |
| 3-hydroxydodecanoic acid | 1% |
| 3-hydroxytetradecanoic acid | 1% |
| 3-hydroxy-5-(2-thienyl) valeric acid | 63% |
| 3-hydroxy-7-(2-thienyl) heptanoic acid | 30% |

What is claimed is:

1. Polyhydroxyalkanoate having monomer unit composition represented by following Chemical Formula [1]:

  [1]

(where, in the above formula, A is at least one expressed by the following Chemical Formula [2]:

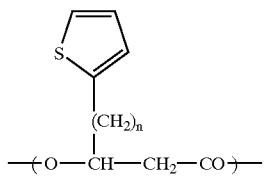  [2]

(n represents any one of integers of 1 to 8);
B is at least one selected from monomer unit expressed by the following Chemical Formula [3]:

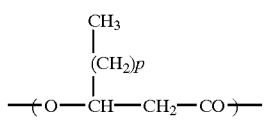  [3]

(where, p represents any one of integers of 0 to 10) or Chemical Formula [4]:

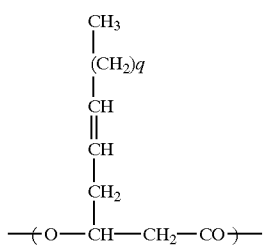  [4]

(where, q is 3 or 5);
and x is a number between or equal to 0.01 and 1).

2. The polyhydroxyalkanoate according to claim 1, comprising monomer unit represented by Chemical Formula [5]:

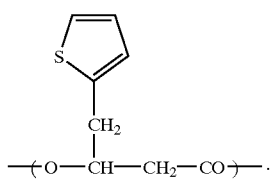  [5]

3. The polyhydroxyalkanoate according to claim 1, comprising monomer unit represented by Chemical Formula [6]:

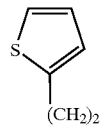  [6]

4. The polyhydroxyalkanoate according to claim 1, comprising monomer unit represented by Chemical Formula [7]:

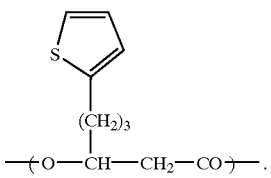  [7]

5. The polyhydroxyalkanoate according to claim 1, comprising monomer unit represented by Chemical Formula [8]:

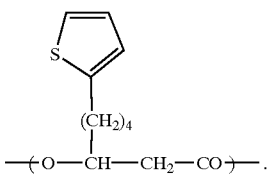  [8]

6. The polyhydroxyalkanoate according to claim 1, comprising monomer unit represented by Chemical Formula [5]:

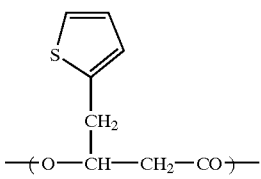  [5]

and also comprising monomer unit represented by Chemical Formula [7]:

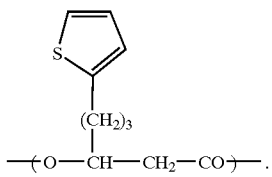

7. The polyhydroxyalkanoate according to claim 1, comprising monomer unit represented by Chemical Formula [6]:

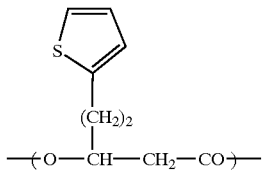

and also comprising monomer unit represented by Chemical Formula [8]:

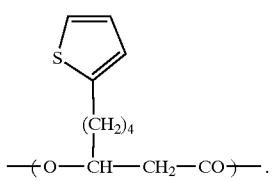

8. The polyhydroxyalkanoate according to claim 1, comprising only monomer unit represented by Chemical Formula [5]:

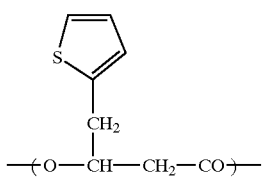

9. The polyhydroxyalkanoate according to claim 1, comprising only monomer unit represented by Chemical Formula [6]:

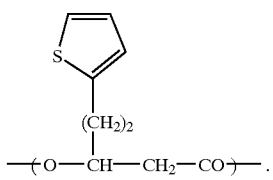

10. The polyhydroxyalkanoate according to claim 1, comprising only monomer unit represented by Chemical Formula [7]:

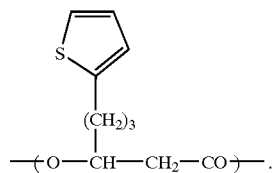

11. The polyhydroxyalkanoate according to claim 1, comprising only monomer unit represented by Chemical Formula [8]:

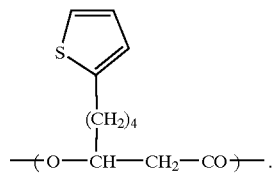

12. The polyhydroxyalkanoate according to claim 1, wherein the number average molecular weight is in the range of 10,000 to 300,000.

13. A method of producing polyhydroxyalkanoate, comprising culturing microorganisms capable of synthesizing polyhydroxyalkanoate having monomer unit composition expressed by the following Chemical Formula [1]:

$$A_x B_{(1-x)} \quad [1]$$

(where, in the above formula, A is at least one expressed by the following Chemical Formula [2]:

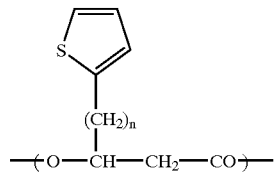

(n is an integer greater than or equal to 1);

B is at least one selected from monomer unit expressed by the following Chemical Formula [3]:

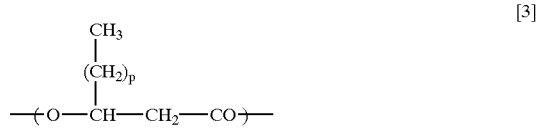

(where, p represents any one of integers of 0 to 10); or Chemical Formula [4]:

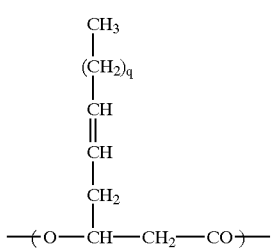

[4]

(where, q is 3 or 5);
and x is a number between or equal to 0.01 and 1) from thienylalkanoic acid using the thienylalkanoic acid, on a culture medium including the thienylalkanoic acid.

14. The method of producing polyhydroxyalkanoate according to claim 13, wherein the thienylalkanoic acid is thienylalkanoic acid expressed by the following Chemical Formula [9]:

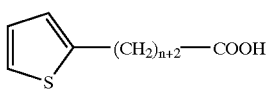

[9]

(n is any one of integers of 1 to 8);
and the polyhydroxyalkanoate is polyhydroxyalkanoate including monomer unit expressed by the following Chemical Formula [10]:

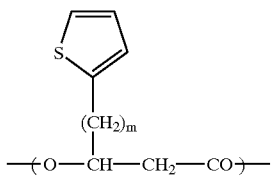

[10]

(where, in the above formula, m is at least one selected from a group consisting of n, n−2, n−4 and n−6, and is an integer greater than or equal to 1).

15. The method of producing polyhydroxyalkanoate according to claim 13, comprising a step of culturing microorganisms for producing polyhydroxyalkanoate having the monomer unit composition by the Chemical Formula [1], using thienylalkanoic acid, on a culture medium including the thienylalkanoic acid and saccharides.

16. The method of producing polyhydroxyalkanoate according to claim 15, wherein the culture of microorganisms is performed in one stage using a culture medium including thienylalkanoic acid and saccharides.

17. The method of producing polyhydroxyalkanoate according to claim 15, wherein the culture of microorganisms is performed in at least two stage with culture using a culture medium including thienylalkanoic acid and saccharides, and following culture using a culture medium including thienylalkanoic acid and saccharides and having reduced nitrogen sources.

18. The method of producing polyhydroxyalkanoate according to claim 15, wherein the saccharides are at least one selected form a group consisting of glucose, fructose and mannose.

19. The method of producing polyhydroxyalkanoate according to claim 13, comprising a step of culturing microorganisms for producing polyhydroxyalkanoate having the monomer unit composition represented by the Chemical Formula [1], using thienylalkanoic acid, on a culture medium including the thienylalkanoic acid and yeast extract.

20. The method of producing polyhydroxyalkanoate according to claim 13, comprising culturing microorganisms for producing polyhydroxyalkanoate having the monomer unit composition represented by the Chemical Formula [1], using thienylalkanoic acid, on a culture medium including the thienylalkanoic acid and polypeptone.

21. The method of producing polyhydroxyalkanoate according to claim 13, further comprising isolating polyhydroxyalkanoate produced by microorganisms.

22. The method of producing polyhydroxyalkanoate according to claim 13, wherein the microorganisms are microorganisms of Pseudomonas sp.

23. The method of producing polyhydroxyalkanoate according to claim 22, wherein the microorganisms are at least one selected from a group consisting of *Pseudomonas putida* P91 (FERM BP-7373), *Pseudomonas cichorii* H45 (FERM BP-7374), *Pseudomonas cichorii* YN2 (FERM BP-7375) and *Pseudomonas jessenii* P161 (FERM BP-7376).

24. The method of producing polyhydroxyalkanoate according to claim 14, comprising culturing microorganisms for producing polyhydroxyalkanoate including monomer unit expressed by the following Chemical Formula [6]:

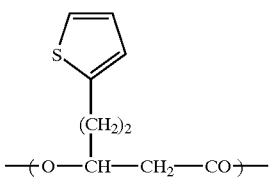

[6]

using 5-(2-thienyl) valeric acid on a culture medium including 5-(2-thienyl) valeric acid expressed by the following Chemical Formula [11]:

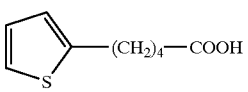

[11]

wherein the produced polyhydroxyalkanoate includes monomer unit expressed by the Chemical Formula [6].

25. The method of producing polyhydroxyalkanoate according to claim 14, comprising culturing microorganisms for producing polyhydroxyalkanoate including monomer unit expressed by the following Chemical Formula [7]:

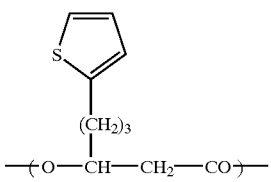

[7]

using 6-(2-thienyl) hexanoic acid on a culture medium including 6-(2-thienyl) hexanoic acid expressed by the following Chemical Formula [12]:

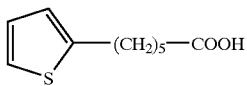

wherein the produced polyhydroxyalkanoate includes monomer unit expressed by the Chemical Formula [7].

26. The method of producing polyhydroxyalkanoate according to claim 14, comprising culturing microorganisms for producing polyhydroxyalkanoate including monomer unit expressed by the following Chemical Formula [8]:

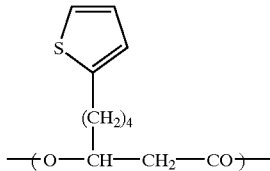

using 7-(2-thienyl) heptanoic acid on a culture medium including 7-(2-thienyl) heptanoic acid expressed by the following Chemical Formula [13]:

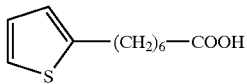

wherein the produced polyhydroxyalkanoate includes monomer unit expressed by the Chemical Formula [8].

27. The method of producing polyhydroxyalkanoate according to claim 14, comprising culturing microorganisms for producing polyhydroxyalkanoate including monomer unit expressed by the following Chemical Formula [5]:

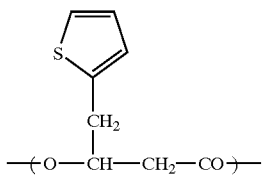

and including monomer unit expressed by the following Chemical Formula [7]:

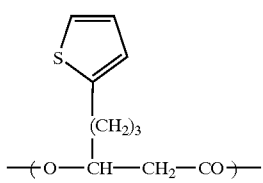

using 6-(2-thienyl) hexanoic acid, on a culture medium including 6-(2-thienyl) hexanoic acid expressed by the following Chemical Formula [12]:

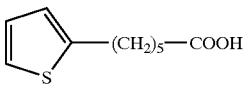

wherein the produced polyhydroxyalkanoate includes monomer unit expressed by the following Chemical Formula [5] and includes monomer unit expressed by the Chemical formula [7].

28. The method of producing polyhydroxyalkanoate according to claim 14, comprising culturing microorganisms for producing polyhydroxyalkanoate including monomer unit expressed by the following Chemical Formula [6]:

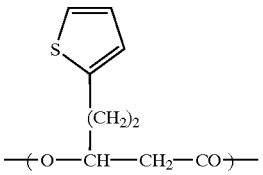

and including monomer unit expressed by the following Chemical Formula [8]:

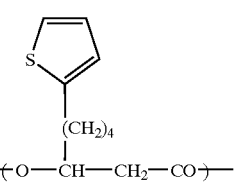

using 7-(2-thienyl) heptanoic acid, on a culture medium including 7-(2-thienyl) heptanoic acid expressed by the following Chemical Formula [13]:

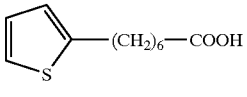

wherein the produced polyhydroxyalkanoate includes monomer unit expressed by the Chemical Formula [6] and includes monomer unit expressed by the Chemical formula [8].

* * * * *

UNITED STATES PATENT AND TRADEMARK OFFICE
CERTIFICATE OF CORRECTION

PATENT NO. : 6,479,621 B2
DATED : November 12, 2002
INVENTOR(S) : Tsutomu Honma et al.

It is certified that error appears in the above-identified patent and that said Letters Patent is hereby corrected as shown below:

Title page,
Item [56], References Cited, U.S. PATENT DOCUMENTS,
"Wiltholt et al." should read -- Witholt et al. --; and
Item [57], ABSTRACT, "extracted and" should read -- extracted. --.

Column 1,
Line 64, "length: abbreviated" should read -- length (abbreviated --.

Column 2,
Line 1, "β oxidation" should read -- β-oxidation --.
Line 22, "routs" should read -- route --; and
Line 58, "hydrates" should read -- hydratase --.

Column 3,
Line 38, "β oxidation" should read -- β-oxidation --.

Column 6,
Line 38, "through β" should read -- through β- --.

Column 10,
Line 56, "THPA" should read -- THpA --.

Column 13,
Line 58, "a enzyme" should read -- an enzyme --.

Column 14,
Line 64, "D-3-hytroxyacyl-" should read -- D-3-hydroxyacyl- --.

Column 15,
In the first figure, "HS—ACP" (second occurrence) should read
-- HS—CoA --.

Column 17,
Line 32, "glucronic" should read -- gluconic --; and
Line 58, "Pseudomonas putida P91," should read -- *Pseudomonas putida* P91, --.

Column 21,
Line 64, "CUSO$_4$:" should read -- CuSO$_4$: --.

UNITED STATES PATENT AND TRADEMARK OFFICE
CERTIFICATE OF CORRECTION

PATENT NO.     : 6,479,621 B2
DATED          : November 12, 2002
INVENTOR(S)    : Tsutomu Honma et al.

It is certified that error appears in the above-identified patent and that said Letters Patent is hereby corrected as shown below:

Column 23,
Line 1, "as a" should read -- as --; and
Line 53, "d: doulet," should read -- d: doublet, --.

Column 27,
Line 21, "quartct," should read -- quartet, --.

Column 34,
Line 47, "THPA," should read -- THpA, --.

Column 41,
Line 63, "form" should read -- from --.

Column 44,
Lines 13 and 56, "formula" should read -- Formula --.

Signed and Sealed this

Eighth Day of July, 2003

JAMES E. ROGAN
*Director of the United States Patent and Trademark Office*